(12) United States Patent
Prokai

(10) Patent No.: US 7,067,257 B2
(45) Date of Patent: Jun. 27, 2006

(54) THYROTROPIN-RELEASING HORMONE ANALOGUES AND THEIR THERAPEUTIC APPLICATIONS

(75) Inventor: Laszlo Prokai, Gainesville, FL (US)

(73) Assignee: University of Florida

( * ) Notice: Subject to any disclaimer, the term of this patent is extended or adjusted under 35 U.S.C. 154(b) by 471 days.

(21) Appl. No.: 10/419,538

(22) Filed: Apr. 21, 2003

(65) Prior Publication Data

US 2003/0232966 A1    Dec. 18, 2003

Related U.S. Application Data

(60) Provisional application No. 60/374,177, filed on Apr. 19, 2002.

(51) Int. Cl.
*A61K 38/00* (2006.01)

(52) U.S. Cl. .......................................................... 435/6
(58) Field of Classification Search ...................... 435/6
See application file for complete search history.

(56) References Cited

U.S. PATENT DOCUMENTS

| | | | |
|---|---|---|---|
| 3,757,003 A | | 9/1973 | Folkers |
| 3,959,248 A | | 5/1976 | Veber et al. |
| 4,305,872 A | * | 12/1981 | Johnston et al. ............ 530/330 |
| 4,562,197 A | | 12/1985 | Snarey et al. |
| 5,244,884 A | | 9/1993 | Spatola et al. |
| 5,405,834 A | | 4/1995 | Bundgaard et al. |
| 5,686,420 A | | 11/1997 | Faden |

FOREIGN PATENT DOCUMENTS

| | | |
|---|---|---|
| EP | 0 473 993 A2 | 3/1992 |
| EP | 0 638 645 A1 | 8/1994 |
| WO | WO 01/60843 A1 | 8/2001 |

OTHER PUBLICATIONS

Attached Structure Search revealing compound formula III species, as disclosed in Johnston et al. (US 4,305,672).*
Bassiri and Utiger, "Metabolism and excretion of exogenous thyrotropin-releasing hormone in humans" *J. Clin. Invest.* 1973, vol. 52, pp. 1616-1619.
Bauer, "Degradation and biological inactivation of thyrotropin releasing hormone (TRH): regulation of the membrane-bound TRH-degrading enzyme from rat anterior pituitary by estrogens and thyroid hormones" *Biochimie.* 1988, vol. 70, pp. 69-74.
Bauer et al., "Specificity of a Serum Peptidase Hydrolyzing Thyroliberin at Pyroglutamyl-Histidine Bond" *Eur. J. Biochem.* 1981, vol. 118, pp. 173-176.
Bycroft et al. "A Novel Lysine-protecting Procedure for Continuous Flow Solid Phase Synthesis of Branched Peptides" *J. Chem. Soc., Chem. Commun.* 1993, p. 778.
Coy et al. "Synthesis and biological properties of the 2-L-beta.-(pyrazolyl-1) alanine analogs of luteinizing hormone-releasing hormone and thyrotropin-releasing hormone" *J. Med. Chem.* 1975, vol. 18, pp. 948-949.
Faden et al. "Thyrotropin-releasing hormone improves neurologic recovery after spinal trauma in cats" *N Eng. J. Med.* 1981, vol. 305, pp. 1063-1067.
Hatanaka et al. "An improved synthesis of thyrotropin releasing hormone (TRH) and crystallization of the tartrate" *Biochem. Biophys. Res. Commun.* 1974, vol. 60, No. 4, pp. 1345-1350.
Horita, "An update on the CNS actions of TRH and its analogs" *Life Sci.* 1998, vol. 62, Nos. 17/18, pp. 1443-1448.
Inanaga et al. "Behavloral effects of protirelin in schizophrenia" *Arch. Gen. Psychiatry* 1978, vol. 35, pp. 1011-1014.
Iversen, "Intra- and extravascular turnover of thyrotrophin-releasing hormone in normal man" *J. Endocrinol.* 1988, vol. 118, pp. 511-516.
Morley, "Extrahypothalamic thyrotropin releasing hormone (TRH)—its distribution and its functions" *Life Sci.* 1979, vol. 25, pp. 1539-1550.
Morley et al. "Plasma clearance and plasma half-disappearance time of exogenous thyrotropin-releasing hormone and pyroglutamyl-N3im-methyl-histidyl prolineamide" *J. Clin. Endocrinol. Metab.* 1979, vol. 48, No. 3, pp. 377-380.

(Continued)

Primary Examiner—Bruce R. Campell
Assistant Examiner—Maury Audet
(74) Attorney, Agent, or Firm—Saliwanchik, Lloyd & Saliwanchik

(57) ABSTRACT

The present invention relates to novel metabolically stable and centrally active TRH analogues and prodrug forms of these analogues, wherein a functional portion of TRH is substituted with a pyridinium moiety or an ester moiety. Methods of synthesis and use of the TRH analogues and associated prodrugs are also provided.

4 Claims, 12 Drawing Sheets

OTHER PUBLICATIONS

Nutt et al. "Synthesis of thyrotropin-releasing hormone analogues with selective central nervous system effects" *J. Med. Chem.* 1981, vol. 24, pp. 692-698.

Prokai et al. "Synthesis and behavioral evaluation of a chemical brain-targeting system for a thyrotropin-releasing hormone analogue" *Eur. J. Med. Chem.* 1998, vol. 33, pp. 879-886.

Prokai et al. "Targeting drugs to the brain by redox chemical delivery systems" *Med. Res. Rev.* 2000, vol. 20, pp. 367-416.

Prokai, "Central nervous system effects of thyrotorpin-releasing hormone and its analogues: opportunities and perspectives for drug discovery and development" *Progress in Drug Research* vol. 59, pp. 136-169.

Prokai et al. "Metabolism-Based Brain-Targeting System for a Thyrotropin-Releasing Hormone Analogue" *J. Med. Chem.* 1999, vol. 42, pp. 4563-4571.

Prokai et al. "Chemical Delivery System To Transport a Pyroglutamyl Peptide Amide to the Central Nervous System" *J. Am. Chem. Soc.* 1994, vol. 116, pp. 2643-2644.

Prokai-Tatrai et al. "Brain-Targeted Delivery of a Leucine-enkephalin Analogue by Retrometabolic Design" *J. Med. Chem.* 1996, pp. 4775-4782.

Schally et al. "Isolation of thyrotropin releasing factoro (TRF) from a porcine hypothalamus" *Biochem. Biophys. Res. Commun.* 1966, vol. 25, No. 2, pp. 165-169.

Schmidt, "Effects of thyrotropine releasing hormone (TRH) on pentobarbital-induced decrease in cholinergic neuronal activity" *Commun. Psycopharmacol.* 1977, vol. 1, pp. 469-473.

Sharp et al. "Analeptic effects of centrally injected TRH and analogues of TRH in the pentobarbitone-anaesthetized rat" *Neuropharmacology* 1984, vol. 23, No. 1, pp. 339-348.

Sobue et al. "Effect of thyrotropin-releasing hormone on ataxia of spinocerebellar degeneration" *Lancet* 1980,. vol. 1, pp. 418-419.

Somlai and Balaspiri, "Synthesis of Analogues of Thyropin-Releasing Hormone" *J. Prakt. Chem.* 1994, vol. 336, p. 525.

Szirtes et al. "Synthesis of thyrotropin-releasing hormone analogues. 1. Complete dissociation of central nervous system effects from thyrotropin-releasing activity" *J. Med. Chem.* 1984, vol. 27, pp. 741-745.

Zincke, et al. "Experimenteller Theil" *Justus Liebigs Ann. Chem.* 1904, vol. 333, p. 296.

Zincke, T. "Allgemeiner Theil" *Justus Liebigs Ann. Chem.* 1903, vol. 330, p. 361.

Chang et al. "Synthesis of Analogs of the Thyrotropin-Releasing Hormone and Structure-Activity Relationships" *Journal of Medicinal Chemistry*, 1971, pp. 484-487, vol. 14, No. 6.

Fraser et al. "A Fertilization Promoting Peptide (FPP)-Related Tripeptide Copetitively Inhibits Responses to FPP: A Cause of Male Subfertility?" *Molecular Reproduction and Development*, 1997, pp. 529-535, vol. 48, No. 4, (Abstract Only).

Mazurov et al. "Synthesis of Peptides by the Method of Mixed Anhydrides in the Presence of Crown Ethers" *Doklady Akademii Nauk SSSR*, 1989, pp. 364-366, vol. 306, No. 2, (Abstract Only).

Prokai-Tatrai et al. "Prodrugs to Enhance Central Nervous System Effects of the TRH-like Peptide pGlu—Glu-Pro-$NH_2$" *Bioorganic & Medicinal Chemistry Letters*, 2003, pp. 1011-1014, vol. 13.

Prokai-Tatrai et al. "Design, Synthesis, and Biological Evaluation of Novel, Centrally0Acting Thyrotropin-Releasing Hormone Analogues" *Bioorganic & Medicinal Chemistry Letters,* 2002, pp. 2171-2174, vol. 12.

* cited by examiner

Legend:

(4) =

(6) =

Legend for FIG. 8 and FIG. 9
1= TRH-Like tripeptide (pGlu-Glu-Pro-NH$_2$)
2A= 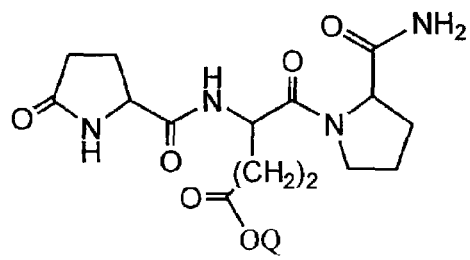 , where Q is Me.
2B= 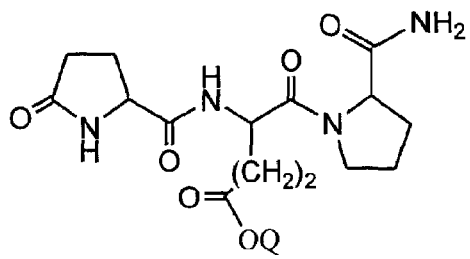 , where Q is Hex.
2C= 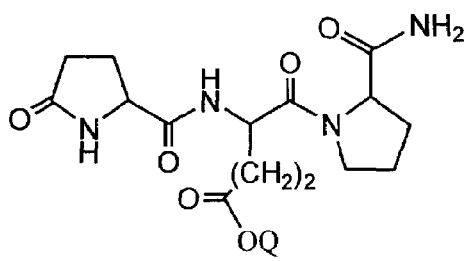 , where Q is cHex.
2D= 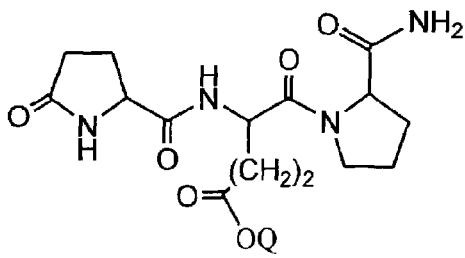 , where Q is tBu.
2E= 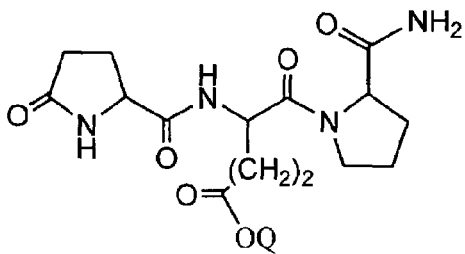 , where Q is Bz.

THYROTROPIN-RELEASING HORMONE ANALOGUES AND THEIR THERAPEUTIC APPLICATIONS

CROSS-REFERENCE TO RELATED APPLICATIONS

This application claims the benefit of U.S. Provisional application No. 60/374,177, filed Apr. 19, 2002.

GOVERNMENT SUPPORT

This invention was made with government support under a grant awarded from the National Institutes of Health under grant number MH59360. The government has certain rights in the invention.

FIELD OF THE INVENTION

The present invention relates to novel analogues of thyrotropin-releasing hormone. In particular, the present invention relates to novel centrally-acting thyrotropin-releasing hormone analogues. The present invention provides thyrotropin-releasing hormone analogues having decreased or absent thyroid stimulating hormone activity and their use as drugs to treat various neurologic and neuropsychiatric disorders.

BACKGROUND OF THE INVENTION

Discovered from the hypothalamus, thyrotropin-releasing hormone (TRH, L-pyroglutamyl-L-histidyl-L-prolinamide) is a peptide that promotes secretion of thyroid stimulating hormone and prolactin of the pituitary glands (Schally, A. V. et al., "Isolation of thyrotropin releasing factor (TRF) from porcine hypothalamus," *Biochem. Biophys. Res. Commun.*, 25(2):165–169 (1966)). Specifically, TRH is a tripeptide with blocked N- and C-terminal residues that is considered common to mammalian species including man, having a structure as shown below:

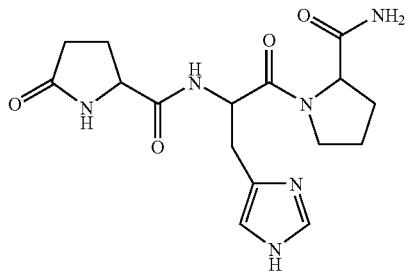

There are three functional portions in the TRH tripeptide structure. The right portion of the molecule is known to those skilled in the art as the "prolineamide" or "C-terminal prolineamide" portion, the center portion of the molecule is known as the "histidyl" or [His$^2$] portion, and the left portion of the molecule is known as the "pyroglutamyl" amino- or "N-terminal" portion.

A major percentage of TRH is released from the hypothalamic nerve terminals in the median eminence to stimulate the secretion of thyroid stimulating hormone. TRH is reported as being widely distributed in almost all sites of the brain and throughout the central nervous system as well as in a variety of tissues, including the alimentary tract, pancreas, placenta, retina of the eye, intestines, and adrenals (Morley, J. E. et al., "Extrahypothalamic thyrotropin releasing hormone (TRH)—its distribution and its functions," *Life Sciences*, 25(18):1539–1550 (1979)).

The distribution of TRH throughout the brain and various organs suggests that TRH plays an important role in the function of the central nervous system and in endocrine-related biological activity. In fact, endogenous TRH is reported as having the ability to act as either a neurotransmitter or a neuromodulator or both.

TRH has recently been shown to antagonize many of the effects of the endogenous opiates in spinal cord injury (Faden, A. I. et al., "Thyrotropin-releasing hormone improves neurologic recovery after spinal traumas in cats," *N. Engl. J Med.*, 305(18):1063–1067 (1981)). The advantage of TRH is that it acts as a physiological opiate antagonist without affecting nociception.

Central or peripheral administration of TRH to organisms has been found to bring about various central nervous actions and behavioral effects in animals (Guillemin, R., *Recent Prog. Horm. Res.*, 33:1–28 (1977)). For example, a central nervous system effect of THR is the "analeptic action," which is the reduction of barbiturate narcosis or haloperidol-induced catalepsy as a measure of cholinergic stimulation (Schmidt, D. E., "Effects of thyrotropine releasing hormone (TRH) on pentobarbital-induced decrease in cholinergic neuronal activity," *Commun. Psychopharm.*, 1(5): 469–73 (1977); Sharp, T. et al., "Analeptic effects of centrally injected TRH and analogues of TRH in the pentobarbitone-anaesthetized rat," *Neuropharmacology*, 23(3): 339–48 (1984); Horita, A., "An update on the CNS actions of TRH and its analogs," *Life Sci.*, 62(17–18):1443–8 (1998)).

Additionally, the administration of TRH has been reported to have therapeutic effect on various disorders and conditions, such as schizophrenia (Inagata, K. et al., "Behavioral effects of protirelin in schizophrenia," *Arch. Gen. Psychiatry*, 35(8):1011–1014 (1978)), melancholia (Hatanaka, C. et al., "An improved synthesis of thyrotropin releasing hormone (TRH) and crystallization of the tartrate," *Biochem. Biophys. Res. Commun.*, 60(4):1345–50 (1974)), spinocerebellar degeneration (Sobue, I. et al., "Effect of thyrotropin-releasing hormone on ataxia of spinocerebellar degeneration," *Lancet*, 1(8165):418–9 (1980)), and neurologic disorders. Improvement of disturbance of consciousness has also been associated with the administration of TRH.

Unfortunately, the clinical utility of TRH has been limited by its rapid metabolism and clearance and poor access to the brain. Due to its highly water-soluble nature and in combination with the absence of specific transport systems in endothelial cells that form the blood-brain barrier (BBB), TRH has poor access to the central nervous system. Moreover, its endocrine effect (i.e., elevation of thyroid hormone levels) is usually manifested at doses in which significant cognitive improvement is observed.

In addition, TRH exhibits a very short biological half-life, roughly 4–6 minutes in rats and humans (Bassiri, R. M. and R. D. Utiger, "Metabolism and excretion of exogenous thyrotropin-releasing hormone in humans," *J. Clin. Invest.*, 52(7):1616–1619 (1973); Morley, J. E. et al., "Plasma clearance and plasma half-disappearance time of exogenous thyrotropin-releasing hormone and pyroglutamyl-N3im-methyl-histidyl prolineamide," *J. Clin. Endocrin. Metab.*, 48, 377–380 (1979); Duntas, L. et al., "Pharmacokinetics and pharmacodynamics of protirelin (TRH) in man," *Dtsch. Med. Wschr.*, 113(35):1354–1357 (1988); Iversen, E., "Intra- and extravascular turnover of thyrotropin-releasing hormone in normal man," *J. Endocrin.*, 118(3):511–516 (1988)) due to rapid degradation by endogenous enzymes, in particular by pyroglutamyl aminopeptidases (Bauer, K. et al., "Specificity of a serum peptidase hydrolyzing thyroliberin at pyroglutamyl-histidine bone," *Euro. J Biochem.*, 118(1): 173–176 (1981); and Bauer, K., "Degradation and biological inactivation of thyrotropin releasing hormone (TRH): regulation of the membrane-bound TRH-degrading enzyme from rat anterior pituitary by estrogens and thyroid hormones," *Biochimie*, 70(1):69–74 (1988)).

The short half-life of TRH is most likely due to rapid degradation of the peptide at both the carboxy (COOH—) and amino ($NH_2$) termini of the TRH molecule. Cleavage of the pyroglutamyl moiety of TRH by peptidases causes formation of the metabolite cyclo-histidyl-proline-diketopiperazine. Deamidation of TRH results in the formation of the free acid TRH-OH.

There have been numerous attempts to produce TRH-like compounds to separate the central nervous system (CNS) and hormonal effects. Analogues where [$His^2$] is replaced by an aliphatic amino acid residue, such as by leucine (Leu) or narvaline (Nva), are characteristic representatives. While these compounds have improved metabolic stability and somewhat higher lipid-solubility compared to TRH, their peptide character prevents them from satisfactory access to the CNS.

Invasive (i.e., by-passing or altering the blood-brain barrier (BBB)) and non-invasive strategies have been developed for improving CNS drug-targeting of hydrophilic drugs such as neuropeptides. A non-invasive strategy is to provide a lipophilic prodrug of a parent drug. Due to improved lipid-solubility, the prodrug may penetrate biological membranes including the BBB and convert the pharmacologically active species at the site of action via predictable enzymatic and/or chemical transformation. Although a lipid-soluble prodrug may assure the diffusion of the parent drug through the BBB, efflux from the CNS is still not prevented if the prodrug cannot be adequately converted into the parent drug at the target site.

Therefore, there is a need for therapeutic agents that are pharmaceutically effective at those regions where they are required. More importantly, there is a need for therapeutic agents that are not rapidly metabolized, effectively penetrate the BBB, are therapeutically active at the blood-CNS interfaces, and do not manifest an unwanted endocrine effect.

BRIEF SUMMARY OF THE INVENTION

The present invention pertains to novel TRH analogues, compositions, and methods for the controlled administration of novel TRH analogues to mammals. The present invention preferably provides centrally active TRH analogues that are metabolically stable, provide enhanced CNS-targeting, and when therapeutically administered, do not manifest unwanted endocrine effect while still providing therapeutically active compounds.

In one aspect of the invention, TRH analogues of the present invention are used for treating diverse physical and neurological conditions such as fatigue, depression, schizophrenia, circulatory shock, amyotrophic lateral sclerosis, spinal cord injury and hypertension. In a further aspect, TRH analogues of the present invention are administered to treat central nervous system disorders such as Alzheimer's disease, brain or spinal cord trauma, and motorneuron disease.

The present invention provides centrally active TRH analogues in which either the histidyl portion, the N-terminal/pyroglutamyl portion, or the C-terminal amide portion of TRH is substituted with pyridinium derivatives. The present invention further includes centrally active TRH analogues in which additional substitutions (i.e., at the histidyl portion) are presented to form negative ions.

In an embodiment, as exemplified herein, TRH analogues are provided in which the histidyl portion of TRH is substituted with a pyridinium derivative. In another embodiment, as exemplified herein, TRH analogues are provided in which the histidyl portion of TRH is substituted with a linker group and carboxyl moiety, sulphonate, or phosphonate. Another embodiment provides TRH analogues in which the N-terminal, pyroglutamyl portion of TRH is modified with pyridinium derivatives. In yet another embodiment, the C-terminal amide of TRH is substituted with pyridinium derivatives to form a quaternary pyridinium compound.

The pyridinium derivative substitutions of the present invention advantageously provide a permanent positive charge to the TRH analogues of the subject invention to enable enhanced nervous system activity, prevent enzymatic degradation, and connote metabolic stability.

In accordance with the present invention, the pyridinium moiety enables the production of prodrugs of TRH analogues via transient chemical modification (i.e., reduction of pyridinium to dihydropyridine). As neutral compounds, the prodrugs of the subject TRH analogues exhibit satisfactory lipophilicity and enable substantially accurate CNS targeting. Additionally, once presented at a target CNS site, the prodrug can be converted so that the pyridinium moiety prevents escape from the target CNS site. Essentially, the pyridinium moiety provides the prodrugs with a positive charge and highly hydrophilic nature. With the formation of the pyridinium moiety (i.e., with endogenous enzymes of the CNS), a TRH analogue of the subject invention is liberated to provide a desired therapeutically effective treatment.

In another embodiment, the present invention provides a novel TRH analogue in which the histidyl portion of TRH is substituted with an ester. Substitution of the histidyl portion of TRH with an ester provides a lipophilic, neutral compound (non-ionizable) that is amenable for diffusion across biological membranes. In a preferred embodiment, these TRH analogues of the present invention can diffuse across tightly connected endothelial cells of the cerebral microcirculation representing the blood-brain barrier.

Once the TRH analogue (histidyl portion substituted with an ester) of the present invention is at a targeted site, the ester is converted into a carboxylic acid via hydrolysis to provide therapeutic activity. The resultant TRH-like tripeptide does not bind to TRH receptors and does not elevate thyroid-hormone (specifically triiodothyronin, $T_3$) levels.

The product of the TRH analogue, once activated endogenously, can exert pharmacological effects through binding to receptors specific for the TRH-like tripeptide in the central nervous system. According to the present invention, the TRH-like tripeptide products of the TRH analogues demonstrate neuroprotective properties as well as analeptic and locomotor activity in the central nervous system. The TRH-like tripeptide product can be used to effectively treat severe unipolar and bipolar depression, schizophrenia, and Parkinson's disease.

Further, the present invention concerns TRH analogues having improved distribution into the central nervous system (CNS), as compared to TRH and currently available TRH analogues. The prodrugs of the TRH analogues of the invention demonstrate enhanced penetration across the blood-brain barrier due to increased lipophilicity and reduction in molecular size.

The TRH analogues of the present invention exhibit decreased or no hormonal activity as compared to TRH and traditional TRH analogues. By replacing the histidyl, pyroglutamyl, or prolineamide portions of TRH, the binding affinity of the subject TRH analogues to TRH receptors is diminished. Thus, the subject TRH analogues demonstrate little or no endocrine activity when administered to affect treatment.

The present invention also provides prodrugs of the above TRH analogues. Prodrugs of the subject TRH analogues can be converted in vivo into biologically active, therapeutic compounds by endogenous enzymes. Thus, the subject prodrugs are advantageous once metabolized and converted into TRH analogues that possess a permanent positive charge and highly lipophilic nature to maintain central nervous system sequestering. Further, prodrug forms of the TRH analogues according to the present invention are designed to overcome problems associated with stability, water-solubility, toxicity, lack of specificity, or limited bioavailability, that exists with TRH and its traditional analogues.

The present invention also concerns prodrugs of the subject TRH analogues having improved blood brain barrier penetration when compared to TRH and traditional TRH analogues. Further, the subject enzymatically oxidized prodrugs are converted into TRH analogues to provide improved neuropharmacodynamic and physiochemical properties when compared to TRH and traditional TRH analogues.

TRH analogues of the present invention can be administered to a patient in a pharmaceutical composition. The pharmaceutical composition preferably includes a therapeutically effective amount of one or more subject TRH analogues in pharmaceutical dosage form to treat and prevent diseases and disorders associated with non-hormone TRH activity. Using the TRH analogues of the present invention results in improved dose administration and a reduction of peaks and troughs characteristic of dosing with TRH. Improved dose administrations potentially result in reduced toxicity of the subject TRH analogues as opposed to TRH and traditional TRH analogues. In addition, pharmaceutical compositions of the present invention including the subject TRH analogues demonstrate increased therapeutic index.

One embodiment of the invention provides pharmaceutical compositions containing prodrug forms of TRH analogues.

The present invention also provides procedures by which the TRH analogues and their prodrugs can be synthesized. In one embodiment, preparatory schemes are provided for the synthesis of prodrug forms of the TRH analogues of the present invention.

In another aspect, the present invention concerns therapeutic methods for the controlled administration of an effective amount of at least one or more of the TRH analogues or prodrug forms of the subject TRH analogues described herein for use in the diagnosis, cure, mitigation, treatment, or prevention of disease or in the enhancement of desirable physical or mental development and conditions in a mammal.

DETAILED DESCRIPTION OF THE INVENTION

Figure 1A:
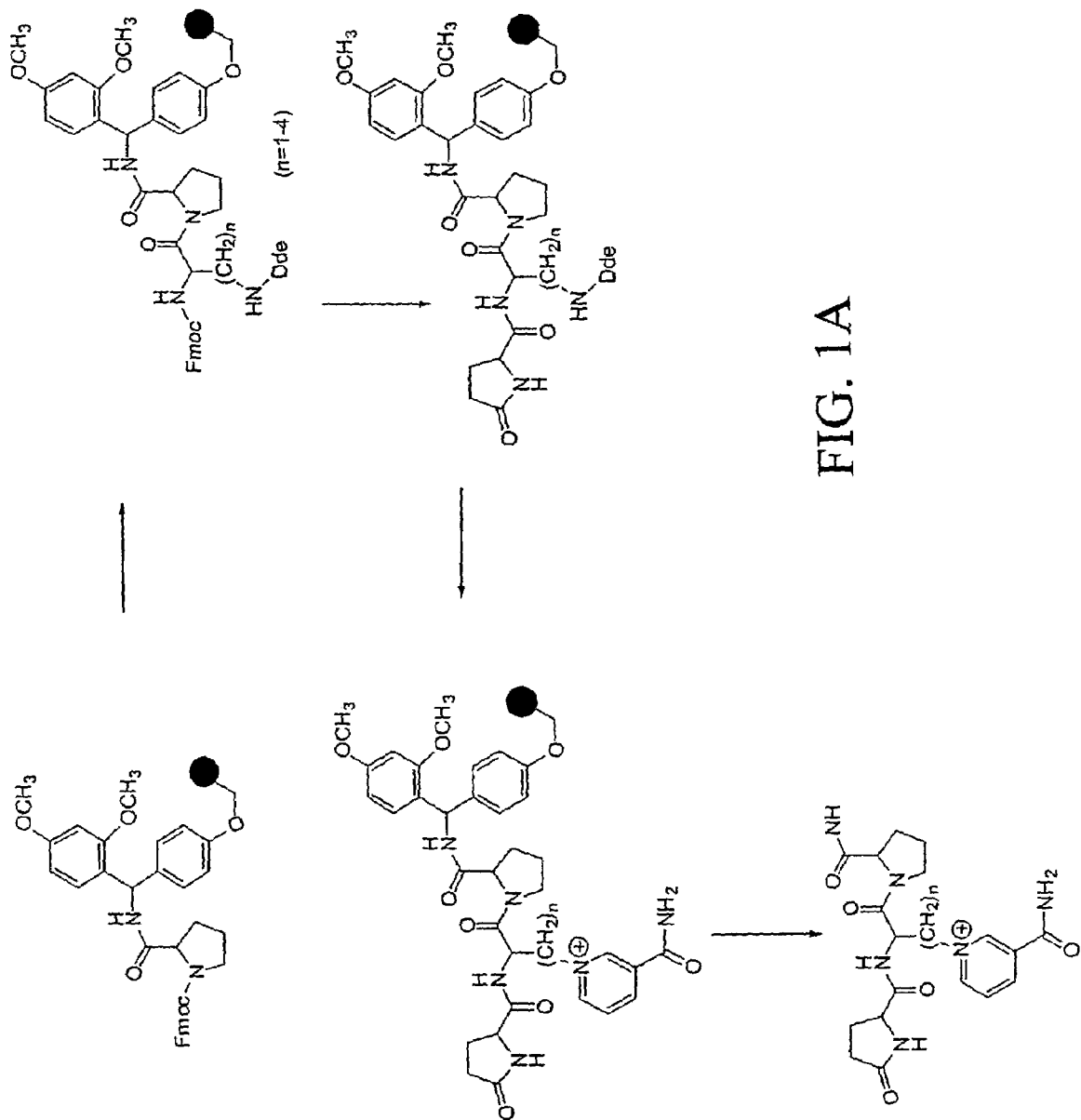
FIGS. 1A, 1B, 1C, and 1D illustrate preparatory schemes for the synthesis of TRH analogues of Formula I according to the present invention.

In accordance with the present invention, certain TRH analogues and prodrug forms of the TRH analogues have been synthesized. Due to the metabolic stability and centrally active characteristics of the subject TRH analogues, their administration as prodrugs is quite advantageous.

The present invention provides TRH analogues wherein either the "prolineamide" (or "C-terminal prolineamide") portion; the "histidyl" (or [His$^2$]) portion; or the "pyroglutamyl" amino- (or "N-terminal") portion of TRH is substituted with pyridinium derivatives. The present invention further includes centrally active TRH analogues in which additional substitutions (i.e., at the histidyl portion) are presented to form negative ions (i.e., phosphonate).

In an embodiment, as exemplified herein, TRH analogues are provided in which the histidyl portion of TRH is substituted with a pyridinium derivative. In another embodiment, as exemplified herein, TRH analogues are provided in which the histidyl portion of TRH is substituted with a linker group and carboxyl moiety, sulphonate, or phosphonate. Another embodiment provides TRH analogues in which the N-terminal, pyroglutamyl portion of TRH is modified with pyridinium derivatives. In yet another embodiment, the C-terminal amide of TRH is substituted with pyridinium derivatives to form a quaternary pyridinium compound.

I. TRH Analogues of the Present Invention

Generally, the present invention concerns TRH analogues of formulas:

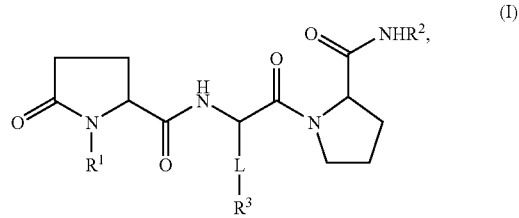

-continued

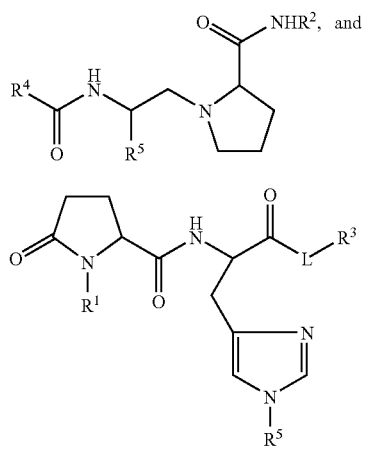

wherein $R^1$ is independently, optionally H, alkyl, aryl, heterocycle, heteroaryl, hydroxyalkyl, alkylaryl, substituted aryl, COX, or COOX, wherein X is alkyl, amine, alkylamino, aryl, substituted aryl, arylalkyl, or acyloxyalkyl;

$R^2$ is optionally H, imidazole, alkyl, aryl, substituted aryl, arylalkyl, CONHCH$_2$COOH, CONHC*H(OH)COOH, CONHC*H(OCOR$^1$)COOH, CONHC*H(OH)COOR$^1$, CONHC*H(OCOR$^1$)COOR$^1$, COX, or COOX, where * is the (S) stereochemical configuration, and where X is as defined above;

$R^3$ is VQ or 3-(R$^1$-)aminocarbonyl-pyridinium-1-yl, where V is COO, sulphonate, phosphonate, or a moiety that provides negative ionic charge, where Q is hydrogen, alkyl, alkyloxycarbonyl, aryl, heterocycle, heteroaryl, alkylamino, hydroxyalkyl, alkoxyalkyl, alkylaryl, substituted aryl, or acyloxyalkyl, and where each member of the pyridinium ring may independently and optionally be substituted with hydrogen, halogen, isopropyl, alkyl, alkenyl, alkynyl, carbocycle, aryl, heterocycle, heteroaryl, alkylamino, hydroxyalkyl, alkoxyalkyl, amide, CN, or a linear or branched hydrocarbon from 1–15 atoms carbon atoms in length, that can optionally include one or more heteroatoms in the chain;

$R^4$ is 1-alkylpyridinium-3-(R$^1$-)aminocarbonyl, 2-alkylisoquinolinium-1-carbonyl, or 2-alkylisoquinolinium-4-carbonyl, where each member of the pyridinium ring, except for the 1-(alkyl) of the pyridinium, the 4-H of the pyridinium, or the 2-(alkyl) of the isoquinolinium, may independently and optionally be substituted with hydrogen, halogen, isopropyl, alkyl, alkenyl, alkynyl, carbocycle, aryl, heterocycle, heteroaryl, alkylamino, hydroxyalkyl, alkoxyalkyl, amide, CN, or a linear or branched hydrocarbon from 1–15 atoms carbon atoms in length, that can optionally include one or more heteroatoms in the chain;

$R^5$ is optionally alkyl, 1-Z, 1H-imidazol-4-ylmethyl (or its tautomeric 1H-imidazol-5-ylmethyl), where Z is optionally H, alkyl, alkyloxycarbonyl, aryl, substituted aryl, arylalkyl, COX, or COOX, wherein X is as defined above; and L is optionally alkyl including (CH$_2$)$_n$, aryl, heterocycle, or heteroaryl, where n is an integer from 0 to 10.

In a preferred embodiment of Formula I, $R^1$ is hydrogen, $R^2$ is hydrogen, and $R^3$ is 3-(R$^1$-)aminocarbonyl-pyridinium-1-yl wherein $R^1$ is CONH$_2$.

In another embodiment of Formula I, $R^1$ and $R^2$ are hydrogen and $R^3$ is COOQ, wherein Q is hexyl.

In a preferred embodiment of Formula II, $R^2$ is hydrogen, $R^4$ is 1-alkylpyridinium-3-(R$^1$-)aminocarbonyl or 2-alkylisoquinolinium-1-carbonyl, and $R^5$ is 1H-imidazol-4-ylmethyl (or its tautomeric 1H-imidazol-5-ylmethyl).

In a preferred embodiment of Formula III, $R^1$ is hydrogen, $R^5$ is tert-butoxycarbonyl, and $R^3$ is 3-(R$^1$)aminocarbonyl-pyridinium-1-yl wherein $R^1$ is CONH$_2$.

II. Definitions

The term "substituted," as used herein, includes multiple degrees of substitution by a named substituent. Where multiple substituent moieties are disclosed, the substituted compound can be independently substituted by one or more of the disclosed or claimed substituent moieties singly or plurally.

Unless otherwise specified, as used herein, the term "alkyl" refers to a straight or branched chain alkyl moiety. In one embodiment, the alkyl moiety is $C_{1-8}$ alkyl, which refers to an alkyl moiety having from one to eight carbon atoms, including for example, methyl, ethyl, propyl, isopropyl, butyl, tert-butyl, pentyl, hexyl, and octyl.

The term "alkyl," as used herein, further includes cyclic alkyl moieties including, for example, cyclopropyl, cyclobutyl, cyclopentyl, cyclohexyl, norbornyl, and adamantyl.

The term "alkyl," as used herein, also refers to alicyclic moieties (also known as cycloalkenyl moieties) having from three to six carbon atoms and having in addition one double bond. Such alicyclic moieties include, for example, cyclopentenyl, and cyclohexenyl.

An alkyl, as defined herein, can be optionally substituted with one or more moieties selected from the group consisting of aryl, heteroaryl, heterocyclic, carbocycle, alkoxy, heterocycloxy, heterocylalkoxy, aryloxy; arylalkoxy; heteroaryloxy; heteroarylalkoxy, carbohydrate, amino acid, amino acid esters, amino acid amides, alditol, halo, haloalkyl, hydroxyl, carboxyl, acyl, acyloxy, amino, amido, alkylamino, dialkylamino, arylamino, nitro, cyano, thiol, imide, sulphonic acid, sulphate, sulphonyl, sulphanyl, sulphinyl, sulphamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulphonamido, carboxamido, hydroxamic acid, sulphonylimide, substituted or unsubstituted urea connected through nitrogen; or any other desired functional group that does not inhibit the pharmacological activity of this compound, either unprotected, or protected as necessary, as known to those skilled in the art, for example, as taught in Greene, et al., Protective Groups in Organic Synthesis, John Wiley and Sons, Second Edition, 1991, hereby incorporated by reference.

The term "alkenyl," as used herein, refers to a straight or branched alkyl moiety having one or more carbon double bonds, of either E or Z stereochemistry (where applicable), and includes for example, vinyl, 1-propenyl, 1- and 2-butenyl, and 2-methyl-2-propenyl.

The term "alkynyl," as used herein, refers to a hydrocarbon that contains at least one carbon-carbon triple bond including, for example, ethynyl, 1-propynyl, 1- and 2-butynyl, 1-methyl-2-butynyl, and the like.

The term "aryl," as used herein, and unless otherwise specified, refers to an aromatic carbocyclic ring including, for example, phenyl, biphenyl, or naphthyl. The aryl group can be optionally substituted with one or more of the moieties selected from the group consisting of alkyl, heteroaryl, heterocyclic, carbocycle, alkoxy, aryloxy, arylalkoxy; heteroaryloxy; heteroarylalkoxy, carbohydrate, amino acid, amino acid esters, amino acid amides, alditol, halo, haloalkyl, hydroxyl, carboxyl, acyl, acyloxy, amino, amido, alkylamino, dialkylamino, arylamino, nitro, cyano, thiol, imide, sulphonic acid, sulphate, sulphonyl, sulphanyl, sulphinyl, sulphamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulphonamido, carboxamido, hydroxamic acid, sulphonylimide or any other desired functional group that does not inhibit the pharmacological activity of this compound, either unprotected, or protected as necessary, as known to those skilled in the art, for example, as taught in Greene, et al., "Protective Groups in Organic Synthesis," John Wiley and Sons, Second Edition, 1991. Alternatively, adjacent groups on the aryl ring may combine to form a 5 to 7 membered carbocyclic, aryl, heteroaryl or heterocylic ring. In another embodiment, the aryl ring is substituted with an optionally substituted cycloalkyl (such as cyclopentyl or cylcohexyl), or an alkylene dioxy moiety (i.e., methylenedioxy).

The term "alkylaryl," as used herein, refers to a moiety in which the "alkyl" and "aryl" groups are as previously described, wherein the alkyl group is linked to the molecule through an aryl group. The alkyl and aryl group can be substituted as described herein.

The term "aralkyl," as used herein, refers to a moiety in which the "alkyl" and "aryl" groups are as previously described, wherein the aryl group is linked to the molecule through an alkyl group. The alkyl and aryl group can be substituted as described herein.

The term "alkylamino," as used herein, refers to a moiety in which the "alkyl" group is as previously described, having at least one $NH_2$ group as a substituent on the molecule. Nonlimiting examples of alkylaminos include, but are not limited to, methylamine, ethylamine, and dimethylamine.

The term "acyl," as used herein, refers to a group of the formula C(O)W, wherein W is an alkyl, aryl, alkylaryl, or aralkyl group, or substituted alkyl, aryl, aralkyl, or alkylaryl, wherein these groups are as defined herein.

The term "amide" or "amido," as defined herein, refers to nonbasic groups generally having the structure —$CONH_2$, —CONHM, or —$CONM_2$, where M is alkyl or substituted alkyl.

The term "amine" or "amino," as defined herein, refers to organic derivatives of ammonia. As readily recognized by the skilled artisan, amines are generally classified as primary, secondary or tertiary, depending on the number of organic substituents attached to the nitrogen.

The term "alkoxy," as used herein and unless otherwise specified, refers to a moiety of the structure —O-alkyl, wherein alkyl is as defined above. The alkyl group can be optionally substituted as described above. Alkoxy groups can include $OCF_3$, $OCH_2CF_3$, $OCF_2CF_3$, and the like.

The term "halogen," as used herein, refers to fluorine, chlorine, bromine, and iodine.

The term "heterocycle," as used herein, refers to a nonaromatic cyclic group that may be partially (contains at least one double bond) or fully saturated and wherein there is at least one heteroatom, such as oxygen, sulfur, nitrogen, or phosphorus in the ring.

The term "heteroaryl," as used herein, refers to an aromatic cyclic group that includes at least one sulphur, oxygen, nitrogen or phosphorus in the aromatic ring.

Nonlimiting examples of heterocyles and heteroaryls include pyrrolidinyl, tetrahydrofuryl, piperazinyl, piperidinyl, morpholino, thiomorpholino, tetrahydropyranyl, imidazolyl, pyrolinyl, pyrazolinyl, indolinyl, dioxolanyl, or 1,4-dioxanyl. aziridinyl, furyl, furanyl, pyridyl, pyrimidinyl, benzoxazolyl, 1,2,4-oxadiazolyl, 1,3,4-oxadiazolyl, 1,3,4-thiadiazole, indazolyl, 1,3,5-triazinyl, thienyl, isothiazolyl, imidazolyl, tetrazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, benzothiazolyl, isothiazolyl, 1,2,4-thiadiazolyl, isooxazolyl, pyrrolyl, quinazolinyl, cinnolinyl, phthalazinyl, xanthinyl, hypoxanthinyl, pyrazole, imidazole, 1,2,3-triazole, 1,2,4-triazole, 1,2,3-oxadiazole, thiazine, pyridazine, or pteridinyl wherein said heteroaryl or heterocycle group can be optionally substituted with one or more substituent selected from the same substituents as set out above for aryl groups. Functional oxygen and nitrogen groups on the heteroaryl group can be protected as necessary or desired. Suitable protecting groups can include trimethylsilyl, dimethylhexylsilyl, tert-butyldimethylsilyl, and tert-butyldiphenylsilyl, trityl or substituted trityl, alkyl groups, acyl groups such as acetyl and propionyl, methanesulphonyl, and p-toluenelsulphonyl.

In one embodiment, the term "heterocycle" includes a partially or fully saturated nonaromatic group including at least one heteroatom, where the heterocycle is bound via an alkyl group. The partially or fully saturated nonaromatic group including at least one heteroatom and the alkyl group can be optionally substituted as described above. In an embodiment, the term "heterocycle" refers to a fully saturated nonaromatic moiety having from two to six carbon atoms and one or more heteroatom from the group nitrogen, oxygen, and sulfur (or oxidized versions thereof) which may be optionally benzofused at any available position. This includes, for example, azetidinyl, pyrrolidinyl, tetrahydrofuranyl, piperidinyl, benzodioxolyl and the like. The term "heterocycle" also refers to an alicyclic moiety having from three to six carbon atoms and one or more heteroatoms from the group nitrogen, oxygen, and sulfur, and having in addition one double bond. Such moieties may also be referred to as "heterocycloalkenyl" and includes, for example, dihydropyranyl, and the like.

In one embodiment, the term "heteroaryl" refers to monocyclic or bicyclic aromatic ring systems of five to ten atoms of which at least one atom is selected from oxygen, nitrogen, and sulfur, in which a carbon or nitrogen atom is the point of attachment, and in which one additional carbon atom is optionally replaced with a heteroatom selected from oxygen or sulfur, and in which from 1 to 3 additional carbon atoms are replaced by nitrogen heteroatoms.

As used herein, the term "centrally active" means a significant pharmacological activity in the central nervous system, often as a result of direct action in the brain.

Neurologic disorders, as used herein, refer to any abnormal central nervous system conditions including, but not limited to, brain and spinal cord trauma; stroke; motorneuron disease; neurodegenerative disorders such as Alzheimer's disease, amyotropic lateral sclerosis, or spinocerebellar degeneration; and coma or stupor due to anesthetics or an overdose of a drug.

The term "patient," describes an animal, including mammals, to whom treatment with the compositions according to the present invention is provided. Mammalian species which benefit from the disclosed methods of treatment include, and are not limited to, apes, chimpanzees, orangutans, humans, monkeys; domesticated animals (e.g., pets) such as dogs, cats, guinea pigs, hamsters, rabbits, and ferrets; and domesticated farm animals such as cows, horses, swine, sheep.

As used herein, the term "prodrug" denotes a molecule which is incapable of exerting the pharmacological activity of the active compound. The active compound will exert its therapeutic effects after it is bioactivated from the transient modified form (i.e., oxidation of the dihydropyridine to pyridinium or hydrolysis of the ester moiety to provide a carboxylic acid). Nonlimiting examples of methods for bioactivating a prodrug contemplated by the present invention include oxidation, reduction, amination, deamination, hydroxylation, dehydroxylation, alkylation, dealkylation, acylation, deacylation, phosphorylation, and dephosphorylation.

The term "pharmaceutically acceptable salt," as used herein, describes any pharmaceutically acceptable form (i.e., ester, mono-, di-, or tri-phosphate ester, salt of an ester or a related group) of a compound of the present invention, which, upon administration to a patient, provides a TRH analogue contemplated by the present invention. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art.

The term "therapeutically effective amount" means that amount of a drug or pharmaceutical agent that will elicit the biological or medical response of a tissue, system, animal or human that is being sought by a researcher, veterinarian, medical doctor or their clinician. In particular, with regard to treating neurologic diseases, conditions and disorders, the "therapeutically effective amount" is intended to mean that amount of the TRH analogue or prodrug of the TRH analogue that will bring about the central nervous action and/or behavioral response that is being sought.

As used herein, the term "treating" refers to preventing, alleviating, retarding, or arresting the progress of either the disorder or condition to which the term "treating" applies, including one or more symptoms of such disorder or condition. The related term "treatment," as used herein, refers to the act of treating a disorder, symptom, or condition, as the term "treating" is defined above.

III. Biological Activity and Therapeutic Applications

The present invention provides TRH analogues that are useful in treating diverse physical and neurological conditions. The TRH analogues of the present invention advantageously provide charged TRH analogues to enable enhanced nervous system activity, prevent enzymatic degradation, and connote metabolic stability.

In accordance with the present invention, TRH analogues including the pyridinium derivative moiety or ester/ion moieties (i.e., sulphonates or phosphonates) can be manipulated to produce of prodrugs of TRH analogues. The prodrugs of TRH analogues of the present invention are provided by chemically rendering ether the pyridinium derivative moieties or ester/ion moieties into neutrally-charged groups. For example, the pyridinium or isoquinolinium group is reduced into neutrally-charged moieties. Such prodrugs exhibit excellent lipophilicity and enable substantially accurate tissue or organ targeting (i.e., in the CNS) for TRH analogue activity.

Once at a target site (i.e., central nervous tissue), the prodrug can be converted to ensure it remains in the target site. In one embodiment, a prodrug of the subject TRH analogue is produced by chemically modifying the pyridinium derivative of a TRH analogue (i.e., pyridinium derivative modified into dihydropyridine). At the target site, the chemically modified portion of the prodrug is converted back into the pyridinium derivative (i.e., enzymatic oxidation). By obtaining a pyridinium moiety, the prodrugs have a permanent positive charge and highly ionic, hydrophilic nature. As such, the obtained pyridinium-prodrug conjugate cannot escape from the target site (i.e., the CNS). To biologically activate the prodrug into the TRH analogues of the present invention, the pyridinium moiety is removed (i.e., by endogenous enzymes) and thus, the therapeutically effective TRH analogues are liberated. An embodiment of the present invention includes the administration of prodrug forms of TRH analogues to the CNS.

After administration of the prodrugs in vivo into the CNS, the dihydro form of the TRH analogues are oxidized in situ by either the NAD$\rightleftharpoons$NADH system or the NAD(P)$\rightleftharpoons$NAD(P)H systems catalyzed by oxidoreductase(s) to promote CNS sequestering. After oxidation, the subject TRH analogues have a permanent positive charge and highly ionic, hydrophilic nature. The positive charge and hydrophilicity enable the subject TRH analogues to be retained in a specific area (i.e., in the brain). Once sequestered, the subject TRH analogues can then be activated with the removal of the pyridinium derivative via enzymatic reactions. The overall result is the therapeutic, CNS-targeted, sustained release of the subject TRH analogues.

The TRH analogues and prodrugs of TRH analogues of the invention can be used alone or in combination with pharmacologically acceptable carriers, additives, or excipients, the proportions of which are determined by solubility and chemical nature of the compound, chosen route of administration, and standard medical practice. In one embodiment of the present invention, pharmaceutical compositions include a therapeutically effective amount of any one or more of the TRH analogues or prodrugs of TRH analogues of the invention in pharmaceutical dosage form to treat and prevent a variety of diseases and disorders, including neurological disorders. The therapeutically effective amount will vary with the condition to be treated, its severity, the treatment regimen to be employed, the pharmacokinetics of the agent used, as well as the patient treated.

The TRH analogues or prodrugs of TRH analogues according to the present invention, whether administered separately or as a pharmaceutical composition of the present invention, can be formulated according to known methods for preparing pharmaceutically useful compositions. Formulations are described in a number of sources that are well known and readily available to those skilled in the art. For example, *Remington's Pharmaceutical Science* (Martin E W [1995] Easton Pa., Mack Publishing Company, 19$^{th}$ ed.) describes formulations, which can be used in connection with the present invention. Formulations suitable for parenteral administration include, for example, aqueous sterile injection solutions, which may contain antioxidants, buffers, bacteriostats, and solutes that render the formulation isotonic with the blood of the intended recipient; and aqueous and nonaqueous sterile suspensions, which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the present invention can include other agents conventional in the art having regard to the type of formulation in question.

The prodrugs of the subject invention provides prolonged beneficial pharmaceutical effects, improved physicochemical properties, improved tissue distribution, increased bioavailability, resistance to metabolic inactivation, and reduced toxicity, in comparison to the highly water-soluble TRH. Due to their lipophilicity, the prodrugs of the present invention can be rapidly transported through the BBB and into the CNS. Prodrug compounds according to the present invention are unique and advantageous.

One embodiment includes prodrug forms of TRH analogues of the present invention wherein the TRH analogue compound includes a pyridinium derivative. The pyridinium derivative connotes a permanent positive charge, making the prodrug of the TRH analogue highly ionic and hydrophilic in nature. The positive charge and hydrophilicity enable the subject TRH analogues to be retained in a specific area (i.e., in the brain). Once sequestered, the subject TRH analogues can then be activated with the removal of the pyridinium derivative via enzymatic reactions. The overall result is the therapeutic, CNS-targeted, sustained release of the subject TRH analogues.

In another embodiment, the prodrug forms of TRH analogues of the present invention include lipophilic dihydro derivatives to furnish CNS targeting. In a preferred embodiment, the TRH analogues include lipophilic dihydropyridine moieties to temporarily alter the compounds so that they are CNS permeable. The lipophilic nature of the prodrugs of the TRH analogues of the invention provides ease of transport through the BBB. Once the prodrug arrives at the target site, a variety of reactions can occur to convert the prodrug into the therapeutically active TRH analogue.

Another embodiment of the present invention provides a TRH analogue in which the histidyl portion of TRH is substituted with an ester group or ion moiety to form a negative ions (i.e., phosphonate, sulphonate). The ester/ion moiety renders the TRH analogue non-endocrine and lipophilic as well as providing a compound that is amenable for diffusion across biological membranes. In a preferred embodiment, the TRH analogue including an ester group can easily diffuse across tightly connected endothelial cells of the cerebral microcirculation representing the blood-brain barrier.

Once the TRH analogue (histidyl portion substituted with an ester) of the present invention is at a targeted site, the ester is converted into a carboxylic acid via hydrolysis to provide therapeutic activity. The resultant TRH-like tripeptide does not bind to TRH receptors and does not elevate thyroid-hormone (specifically triiodothyronin, $T_3$) levels.

Tissues that may be therapeutically treated with subject TRH analogues or prodrugs of the TRH analogues may be derived from children, adult or fetuses and include, but are not limited to, central nervous tissue, including brain and spinal cord tissue, neurons, and glia; peripheral nervous tissue, including ganglia, posterior pituitary gland, adrenal medulla, and pineal.

The subject TRH analogues and prodrug forms of the TRH analogues are therapeutic in the diagnosis, cure, mitigation, treatment, or prevention of disease or in the enhancement of desirable physical or mental development and conditions in a mammal. According to the present invention, the TRH analogues can be used to improve memory and learning. Further, TRH analogues of the present invention can be used in treating diverse physical and neurological conditions such as fatigue, depression, schizophrenia, circulatory shock, amyotrophic lateral sclerosis, and hypertension. Examples of diseases, disorders and conditions that may be treatable by a TRH analogue or prodrug form of the present invention include: mental disorders including depression, dementia, and schizophrenia; encephalomyelitis including Chronic Fatigue Syndrome; brain diseases including leukodystrophy, adrenoleukodystrophy, migraines, epilepsy, Alzheimer's disease, Parkinsonian disorders, cerebral palsy, and Huntington disease; brain or spinal cord trauma (i.e., stroke, brain hypoxia); and motorneuron diseases/disorders including Tourette Syndrome. The preceding list of diseases and conditions which are potentially treatable with the subject TRH analogues or associated prodrugs is not intended to be exhaustive or limiting but presented as examples of such degenerative diseases and conditions.

Pharmaceutical compositions based upon these TRH analogues may be formulated for a variety of routes of administration, including, for example, orally-administrable forms such as tablets, capsules or the like, or via parenteral, intravenous, intramuscular, transdermal, buccal, subcutaneous, suppository, or other route. In certain pharmaceutical dosage forms, certain of the present TRH analogues may be more appropriate than other compounds, depending upon the route of administration and the targeted site within the patient. The compositions of the invention can be formulated so as to provide quick, sustained or delayed release of the active ingredient after administration to the patient by employing procedures known in the art.

The compounds of the present invention may be administered in a pharmaceutical composition comprising the TRH analogue or prodrug of the TRH analogue in combination with a pharmaceutically acceptable carrier adapted for topical administration. Topical pharmaceutical compositions may be in the form of a solution, cream, ointment, mousse, gel, lotion, powder or aerosol formulation adapted for application to the skin.

Topical preparation containing the TRH analogues or prodrugs of TRH analogues of the subject invention can be admixed with a variety of carrier materials or pharmaceutically acceptable excipients well known in the art. When the excipient serves as a diluent, it can be a solid, semi-solid, or liquid, which acts as a vehicle, carrier or medium for the active ingredient. Thus, the compositions can be in the form of powders, suspensions, emulsions, solutions, syrups, alcoholic solutions, ointments, topical cleansers, cleansing creams, skin gels, skin lotions, mousses, roll-ons, aerosol or non-aerosol sprays in cream or gel formulations and soft gelatin capsules Therapeutic methods according to the present invention include the controlled administration to a patient of an effective amount of at least one or more of the TRH analogues as set forth above to provide therapy. Administration to a patient may range from continuous (intravenous drip) to intramuscular, to several oral administration per day (for example, Q.I.D.) and may include parenteral, including intravenous and intramuscular, oral, topical, subcutaneous, transdermal (which may include a penetration agent), buccal and suppository administration, among other routes of administration.

To prepare the pharmaceutical compositions according to the present invention, a therapeutically effective amount of one or more of the compounds according to the present invention is preferably intimately admixed with an optional pharmaceutically acceptable carrier according to conventional pharmaceutical compounding techniques to produce a dose. A carrier may take a wide variety of forms depending on the form of preparation desired for administration, e.g., oral or parenteral.

For parenteral formulations, the carrier may comprise sterile water or aqueous sodium chloride solution in combination with other ingredients that aid dispersion, such as ethanol and other pharmaceutically acceptable solvents. Of course, where solutions are to be used and maintained as sterile, the compositions and carrier must also be sterilized. Injectable suspensions may also be prepared, in which case appropriate liquid carriers, suspending agents and the like may be employed.

In preparing pharmaceutical compositions in oral dosage form according to the present invention, any one or more of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, tablets or capsules may be entericcoated or sustained release by standard techniques.

The TRH analogues of the present invention may be prepared using known reagents and reactions, including for example, TRH-like tripeptide pGlu-Glu-Pro-NH$_2$, Fmoc-Pro-Rink-4-methylbenzydryl-amine, tert-butyloxycarbonyl amino acids, 9-fluorenylmetoxycarbonyl amino acids, or the like. The following Example 1 is exemplary and provided for purposes of illustration and are not intended to be limitative.

Abbreviations

The abbreviation "ACh" as used herein refers to acetylcholine.

The abbreviation "APCI" as used herein refers to atmospheric-pressure chemical ionization.

The abbreviation "BBB" as used herein refers to the blood-brain barrier.

The abbreviation "Boc" as used herein refers to tert-butyloxycarbonyl.

The abbreviation "Bz" as used herein refers to benzoyl.

The abbreviation "cHex" as used herein refers to a cyclohexyl group.

The abbreviation "CNS" as used herein refers to the central nervous system.

The abbreviation "CPP" as used herein refers to a CNS-permeable prodrug.

The abbreviation "DCM" as used herein refers to dichloromethane.

The abbreviation "Dde" as used herein refers to (1-(4,4-dimethyl-2,6-dioxocyclohex-1-ylidene)ethyl).

The abbreviation "DIPEA" as used herein refers to diisopropylethylamine.

The abbreviation "DMF" as used herein refers to dimethylformamide.

The abbreviation "DMSO" as used herein refers to dimethyl sulphoxide.

The abbreviation "ESI" as used herein refers to electrospray ionization.

The abbreviation "EtOAc" as used herein refers to MeOH/ethyl acetate.

The abbreviation "Fmoc" as used herein refers to 9-fluorenylmethyloxycarbonyl.

The abbreviation "Hex" as used herein refers to a hexyl group.

The abbreviation "HOBt" as used herein refers to N-hydroxy-benzotriazole.

The abbreviation "HPLC" as used herein refers to high performance liquid chromatography.

The abbreviation "IAMC" as used herein refers to immobilized artificial membrane chromatography.

The abbreviation "i.p." as used herein refers to intraperitoneal.

The abbreviation "i.v." as used herein refers to intravenous.

The abbreviation "logD" as used herein refers to the logarithm of n-octanol/water distribution coefficient (for ionic compounds).

The abbreviation "logP" as used herein refers to the logarithm of n-octanol/water partition coefficient.

The abbreviation "Me" as used herein refers to methyl group.

The abbreviation "MeOH" as used herein refers to methanol.

The abbreviation "MBHA" as used herein refers to methylbenzydryl-amine.

The abbreviation "Mtt" as used herein refers to 4-methyltrityl.

The abbreviation "PyBOP) as used herein refers to benzotriazole-1-yl-oxy-tris-pyrrolidino-phosphonium hexafluorophosphate.

The abbreviation "SPPS" as used herein refers to solid-phase peptide synthesis.

The abbreviation "tBu" as used herein refers to a tert-butyl group.

The abbreviation "TFA" as used herein refers to trifluoroacetic acid.

The abbreviation "TRH" as used herein refers to thyrotropin-releasing hormone.

The abbreviation "UV" as used herein refers to ultraviolet radiation.

The abbreviation "Xaa" as used herein refers to an amino acid residue.

The following examples are preparatory schemes, according to the present invention, for TRH analogues of Formulas I, II, and III, including preparatory schemes for their associated prodrugs.

EXAMPLE 1

Synthesis of TRH Analogue of Formula I

As illustrated in FIG. 1A, pre-loaded Fmoc-Pro-Rink Amide-MBHA resin was deprotected with 20% (v/v) piperidine in DMF for 10 minutes, followed by coupling with Fmoc-diaminopropionic/butyric acid, ornithine, or lysine, respectively, protected with Dde (B. Bycroft, et al., *J. Chem. Soc. Chem. Commun.*, 778 (1993))in their side-chain amino group. Once the pyroglutamic acid had been attached, the Dde group was removed by two 5 minute treatments of the resin with 2% hydrazine hydrate in DMF unmasking the side chain amino group for the Zincke-reaction. A Zincke-type salt [N-(2,4-dinitrophenyl)nicotinamide chloride] was initially prepared by heating the mixture of 1-chloro-2,4-dinitrobenzene (1.1 eq) and nicotinamide (1 eq) at 100° C. for 2 hours. After cooling down, MeOH was added and the product was precipitated with ether. This procedure was repeated 3 times. Recrystallization from EtOAc resulted in a pale-yellow solid. To the resin suspended in DMF, 5 eq. of the Zincke-type salt was added in the presence of catalytic amount of pyridine and the mixture was kept at 60° C. The reaction was usually complete within 4–5 hours. TRH analogues according to the present invention are cleaved from the resin using TFA:water (98:2, v/v) and purified by semi-preparative gradient, HPLC on octadecylsilica reversed phase. The completion of the reaction may be monitored by HPLC with UV detection at 254 nm.

Figure 1B:
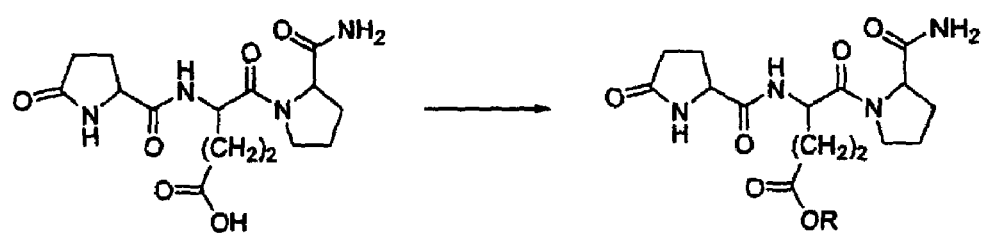
Figure 1C:
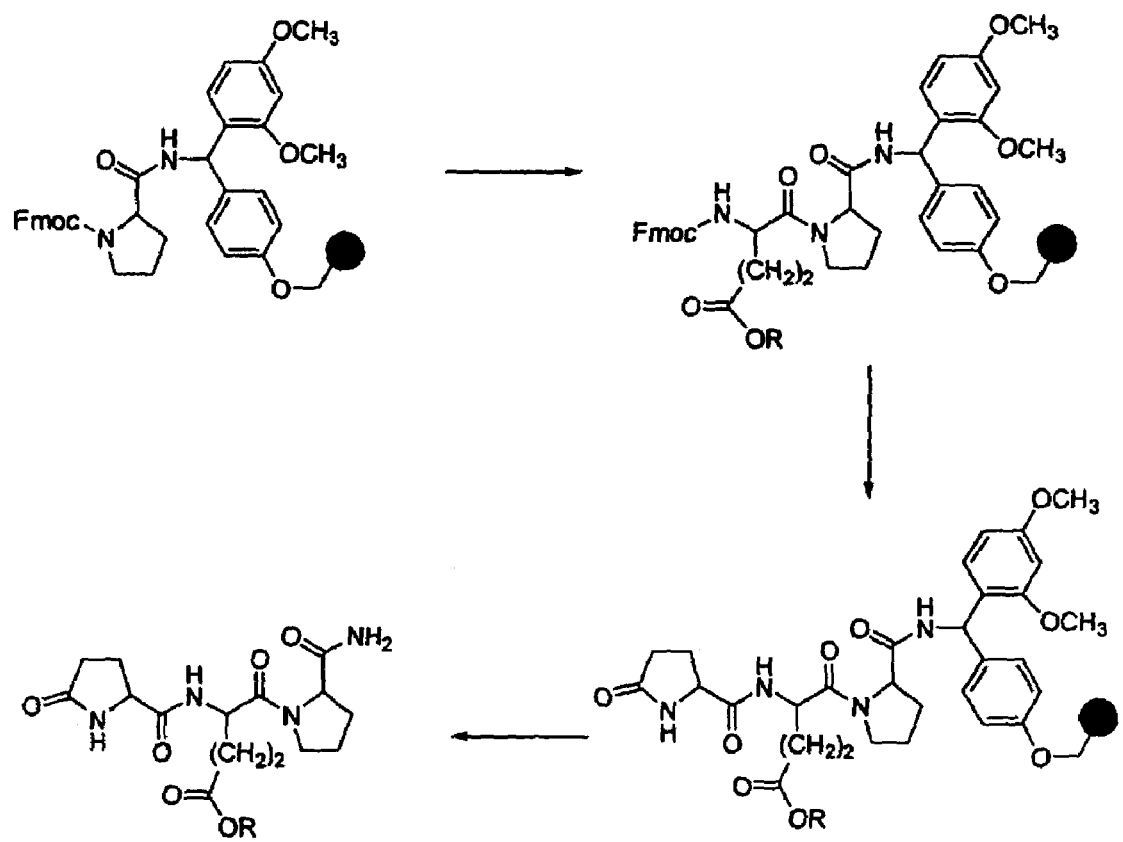
Figure 1D:
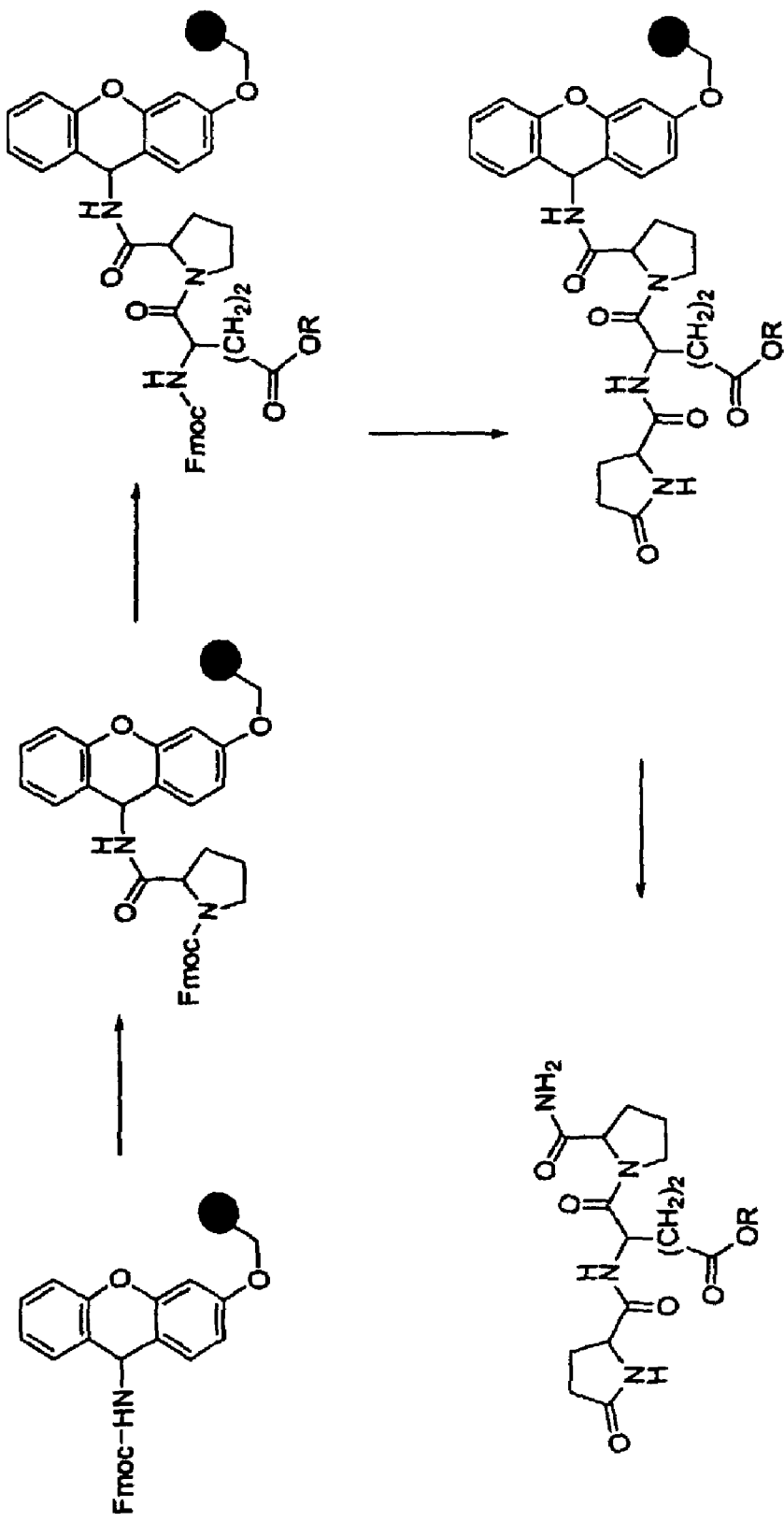

FIGS. 1B, 1C, and 1D illustrate preparatory schemes for producing TRH analogues of Formula I in which the histidyl portion is substituted with an ester group. In FIG. 1B, a TRH analogue of the present invention is provided by overnight direct esterification of TRH-like tripeptide pGlu-Glu-Pro-NH$_2$ in the presence of N-cyclohexylcarbodiimide (3 eq), N'-methyl polystyrene (loading: 1.3 mmole/g), and N-(methylpolystyrene)-4-(methylamino)pyridine (loading: 1.49 mmole/g) in DCM using 5-fold excess of alcohol (5 eq). The resultant TRH analogue of the present invention is provided in nearly quantitative yield.

Alternatively, SPPS can be used in preparing TRH analogues of Formula I in which the histidyl portion is substituted with an ester group. For example, in FIG. 1C, preloaded Fmoc-Pro-Rink-4-MBHA resin was deprotected with 20% (v/v) piperidine in DMF for 10 minutes followed with PyBOP:HOBt:Fmoc-Glu(R):DiPEA (1:1:1:2). The resultant compound was deprotected with 20% (v/v) piperidine in DMF for 10 minutes then treated with PyBOP:HOBt:pyroglutamic acid:DiPEA (1:1:1:2). TRH analogues according to the present invention are cleaved from the resin using TFA:water (98:2, v/v) and purified by semi-preparative gradient, HPLC on octadecylsilica reversed phase. The completion of the reaction may be monitored by HPLC with UV detection at 254 nm.

In FIG. 1D, super acid-sensitive Sieber Amide resin was loaded with Fmoc-Pro utilizing standard PyBOP/DiPEA procedure (i.e., deprotection with 20% (v/v) piperidine in DMF for 10 minutes followed by treatment with PyBOP:HOBt:pyroglutamic acid:DiPEA (1:1:1:2)). The resultant compound was deprotected with 20% (v/v) piperidine in DMF for 10 minutes followed with PyBOP:HOBt:Fmoc-Glu(R):DiPEA (1:1:1:2), deprotection with 20% (v/v) piperidine in DMF for 10 minutes, then treatment with PyBOP:HOBt:pyroglutamic acid:DiPEA (1:1:1:2). TRH analogues according to the present invention are cleaved from the resin using TFA:water (98:2, v/v) and purified by semi-preparative gradient, HPLC on octadecylsilica reversed phase. The completion of the reaction may be monitored by HPLC with UV detection at 254 nm.

EXAMPLE 2

Synthesis of Prodrugs of TRH Analogues of Formula I

Figure 2:
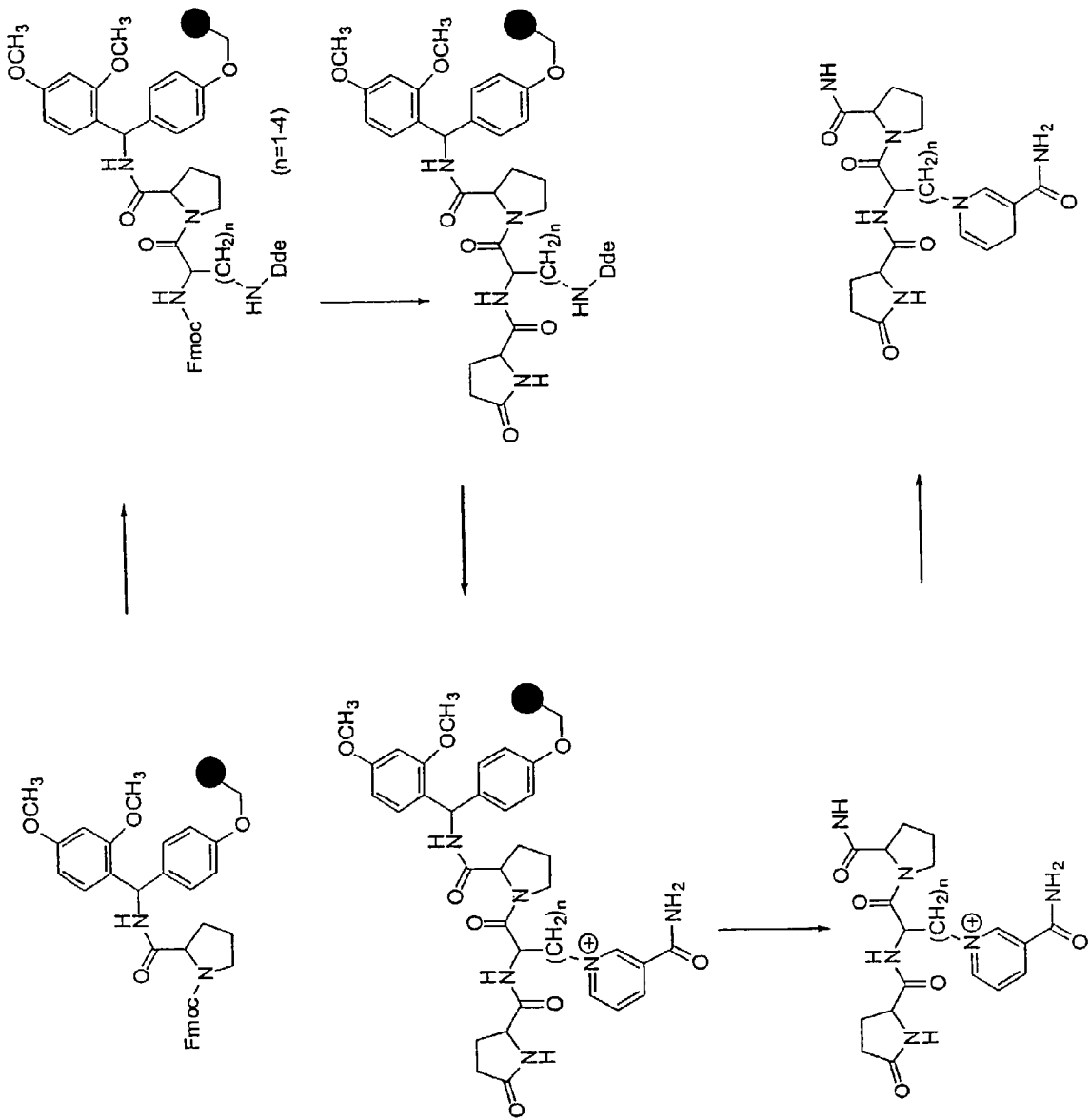
FIG. 2 illustrates a preparatory scheme for the synthesis of prodrugs of TRH analogues of Formula I according to the present invention.

FIG. 2 illustrates the preparation of prodrugs of TRH analogues of Formula I produced via SPPS synthesis utilizing Fmoc-chemistry. Prodrugs of TRH analogues of Formula I are obtained by reducing the TRH analogues with Na$_2$S$_2$O$_4$ in water, pH 7. The completion of the reaction may be monitored by HPLC with UV detection at 355 nm.

EXAMPLE 3

Synthesis of TRH Analogues of Formula II Using Semi-Automated Solid Phase Peptide Synthesis (SPPS)

Figure 3A:
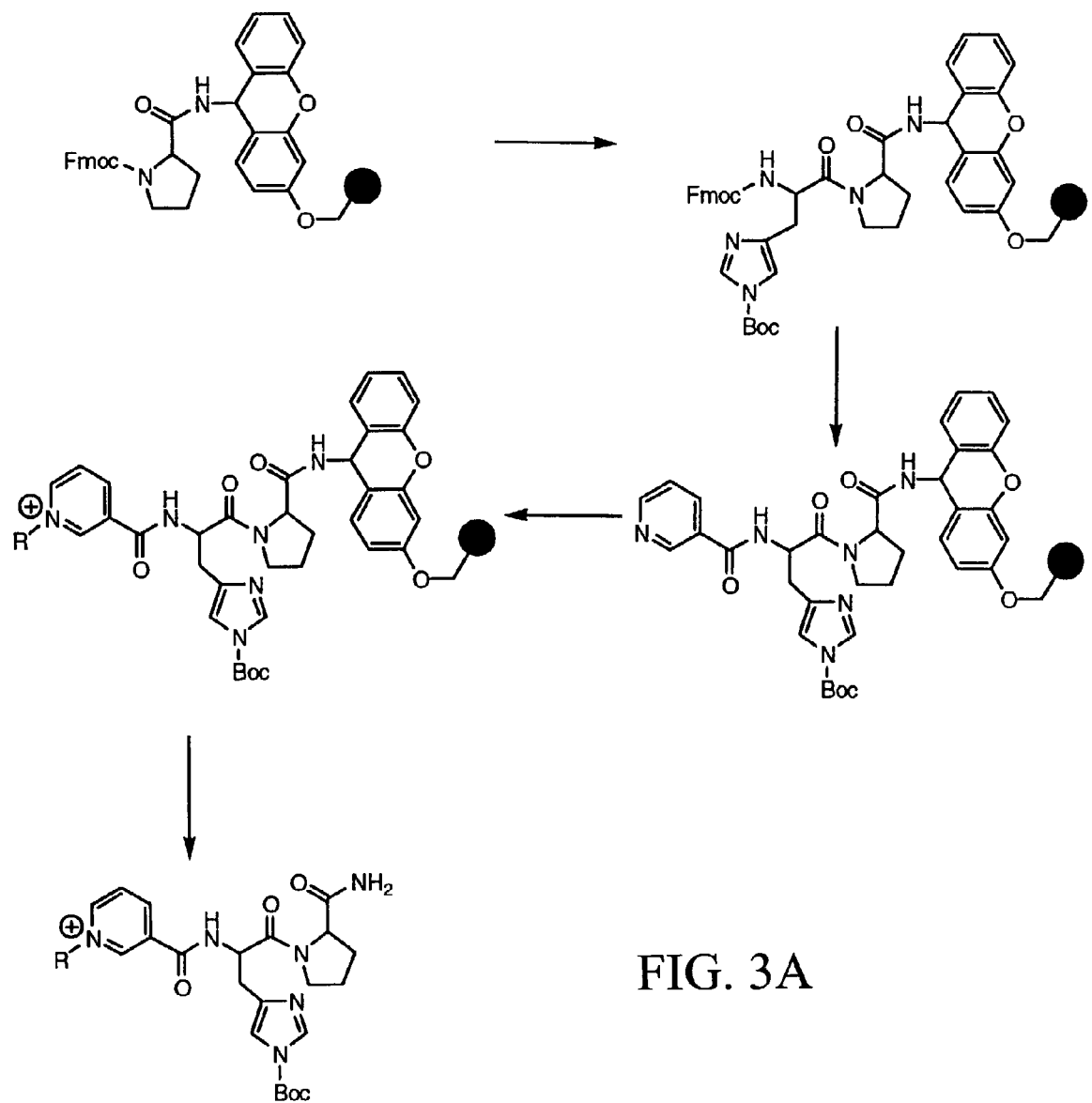
FIGS. 3A, 3B, and 3C illustrate preparatory schemes for the synthesis of TRH analogues of Formula II and their prodrugs according to the present invention.

As illustrated in FIG. 3, pre-loaded Fmoc-Pro-Sieber Amide resin is deprotected by 20% (v/v) piperdine in dimethylformamide (DMF), then Fmoc-His(Boc)-OH (or Fmoc-Xaa) is coupled using PyBOP/HOBt/DIPEA (1:1:2) activation. After the removal of the Fmoc-protecting group, the peptide chain is terminated using nicotinic (isonicotinic/quinolic/isoquinolic) acid. As is understood by the skilled artisan, a double-coupling may also be applied. The pyridine moiety of the resin-bound peptide is alkylated with alkyl halide/p-toluenesulphonate in DMF for two (2) hours. After washing and drying the resin, a TRH analogue of Formula II is obtained by cleaving the compound from the resin using 1% (v/v) TFA in DCM. The completion of the reaction may be monitored by HPLC with UV detection at 254 nm.

Figure 3B:
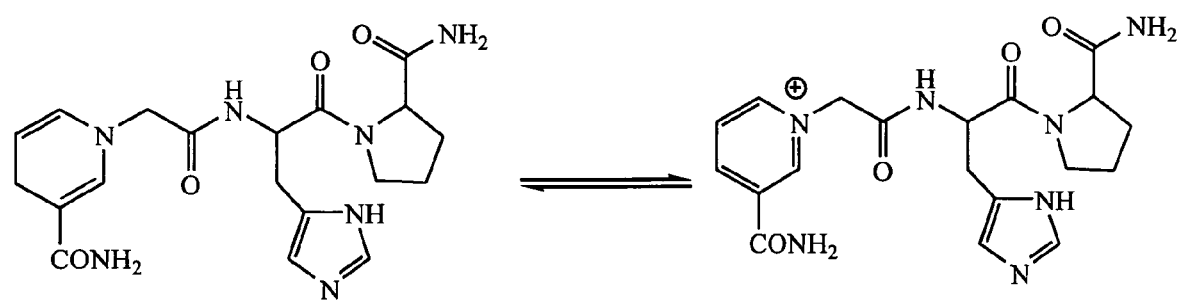
Figure 3C:
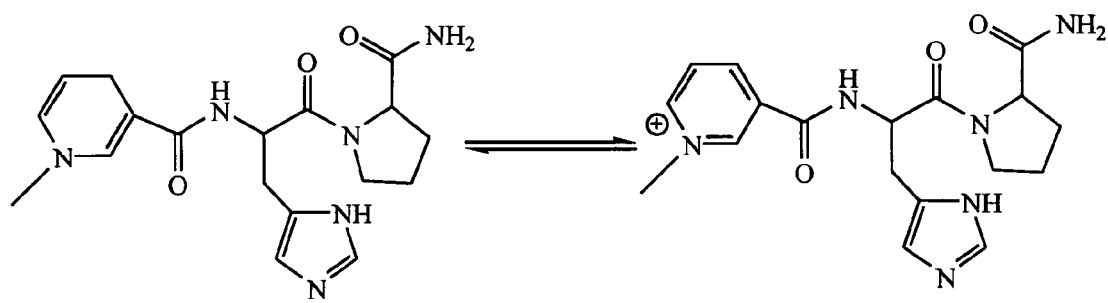

Synthesis of additional TRH analogues of Formula II and corresponding prodrugs, as illustrated in FIGS. 3B and 3C, were also performed using the solid-phase peptide synthesis (SPPS) strategy.

To synthesize the TRH analogue of Formula II illustrated in FIG. 3B, a peptide chain built on a solid support analogous to TRH is provided. Upon attaching Fmoc-glycine to the central histidine, the Fmoc was removed by the standard procedure and a solid-phase Zincke reaction was then applied. The resin was suspended in DMF (1 g/30 ml) and 5 eq [N-(2,4-dinitrophenyl)nicotinamide chloride] was added together with 3 eq triethylamine and catalytic amount of pyridine. [Zincke-salt N-(2,4-dinitrophenyl)nicotinamide chloride was prepared by heating the mixture of 1-chloro-2,4-dinitrobenzene (1.1 eq) and nicotinamide (1 eq) at 100° C. for 2 hours]. After cooling down, MeOH was added and the product was precipitated with ether. This procedure was repeated 3 times. Recrystallization from MeOH/EtOAc resulted in a pale-yellow solid, m.p. 186–187° C.) The reaction mixture was agitated at elevated temperature (50–60° C.). The progress of the Zincke-reaction was monitored by the ninhydrine test and/or by ESI-MS after cleaving small amount of peptide from a couple of beads removed as samples. The color change of the solvent (from red to yellow) can be used as an indicator for the product formation. Upon completion of the amine→pyridinium exchange, the resin was thoroughly washed with MeOH, DMF and DCM. The product was removed from the solid support by TFA:water [98:2 (v/v), 1 g resin/10 ml, 4 hours]. Nitrogen stream was used to concentrate the solution. The oily residue was washed several times with diethyl ether and the solid obtained was subjected to RP-HPLC purification. After freeze-drying the combined chromatographic fractions containing the product, the purity of the peptide was verified by analytical RP-HPLC. MS (ESI): m/z 414 (C$^+$).

To synthesize the TRH analogue of Formula II illustrated in FIG. 3C, SPPS utilizing standard Fmoc-chemistry with PyBOP/HOBt/DIPEA (1:1:2) activation on a semi-automated peptide synthesizer was used. The synthesis started with Fmoc-group removal of the preloaded Fmoc-Pro-Rink-MBHA-Amide resin (Bachem BioSciences (Torrance, Calif.) by 20% (v/v) piperidine in DMF for 10 minutes. Fmoc-His(3-Boc)-OH was then attached. The chain was terminated with trigonelline hydrochloride (1-Methylpyridinium-3-carboxylate hydrochloride, Aldrich Chem. Co. (Milwaukee, Wis.). The use of nicotinic acid and subsequent methylation can be avoided because, independently from the type of imidazole protecting group in position 3, a parallel 1-methylation is significant and the separation of the desired product from the bismethylated side-product is cumbersome. The product was removed from the solid support by TFA: water [98:2 (v/v), 1 g resin/10 ml, 4 hours]. Nitrogen stream was used to concentrate the solution. The oily residue was washed several times with diethyl ether and the solid obtained was subjected to RP-HPLC purification. After freeze-drying the combined chromatographic fractions containing the product, the purity of the peptide was verified by analytical RP-HPLC. MS (ESI): m/z 371 (C$^+$).

General methods for synthesizing prodrugs of the TRH analogues of Formula II are also illustrated in FIGS. 3B and 3C. Under continuous purging of the reaction vessel with nitrogen gas, the TRH analogue of FIG. 3B and FIG. 3C was dissolved, respectively, in 50% (v/v) aqueous MeOH and then sodium dithionite (10 eq) was added together with enough sodium bicarbonate to adjust the pH to 6.5–7.0. The progress of the reduction was monitored by UV-spectrophotometry (254 nm for the TRH analogues in FIGS. 3B and 3C, and 350 nm for the prodrugs of the TRH analogues illustrated in FIGS. 3B and 3C). Once the reduction was completed (usually within 2 hours) the reaction mixture was extracted (3×) with cold, degassed DCM. The solvent was then removed in vacuo and the residual product was subjected to analytical HPLC analysis before administering it to the experimental animals. If the purity of the prodrug was not satisfactory, column chromatographic purification was applied on neutral alumina using DCM:MeOH (9:1, v/v) eluent. MS (APCI) m/z 416 [M+H]$^+$ for the prodrug illustrated in FIG. 3B; m/z 373 [M+H]$^+$ for the prodrug illustrated in FIG. 3C.

EXAMPLE 4

Synthesis of Prodrugs of TRH Analogue of Formula II

Figure 4:
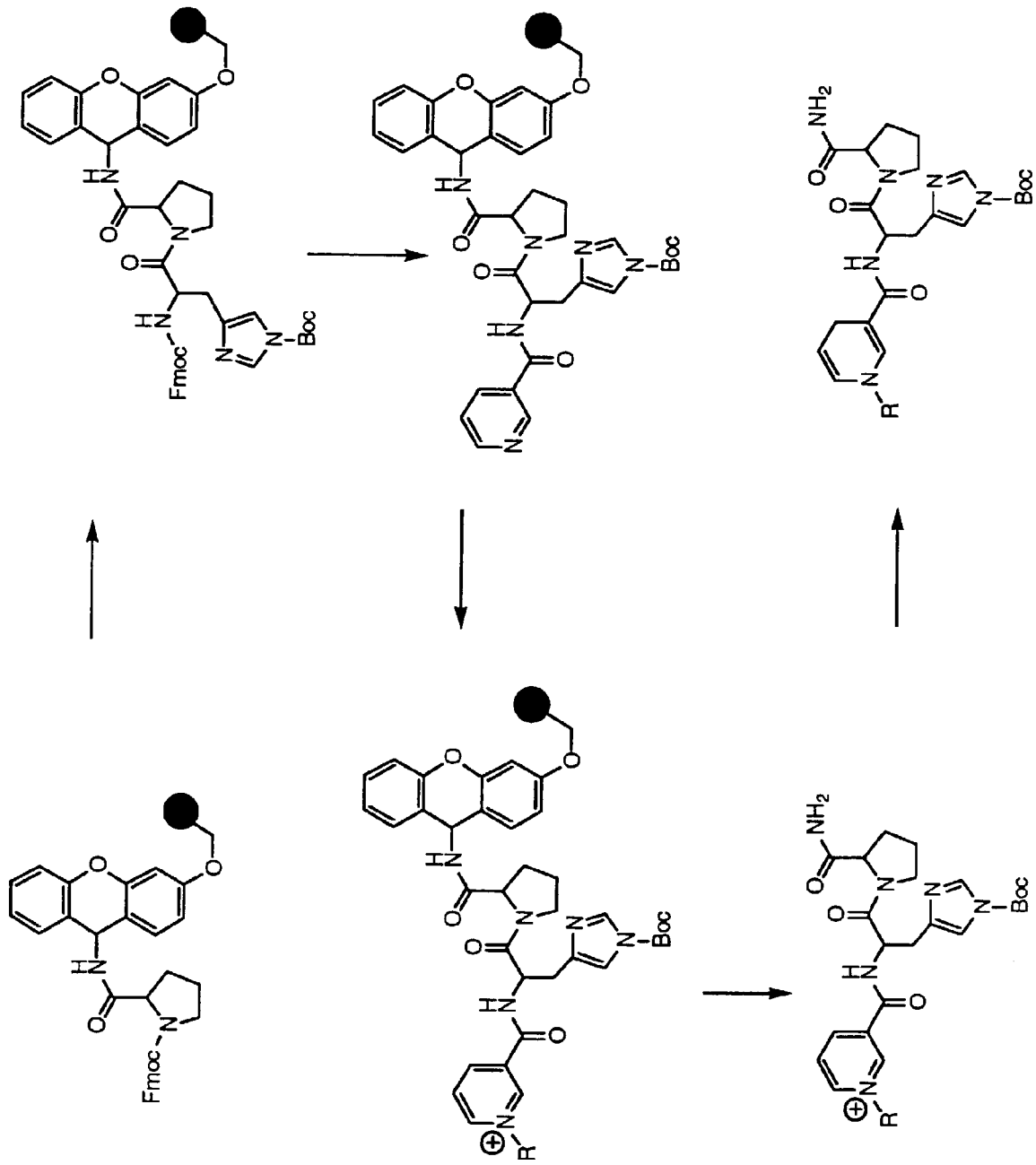
FIG. 4 illustrates a preparatory scheme for the synthesis of prodrugs of TRH analogues of Formula II according to the present invention.

FIG. 4 illustrates the preparation of prodrugs of TRH analogues of Formula II produced via SPPS synthesis utilizing Fmoc-chemistry. Prodrugs of TRH analogues of Formula II are obtained by reducing the TRH analogues with $Na_2S_2O_4$ in water, pH 7. The completion of the reaction may be monitored by HPLC with UV detection at 355 nm.

EXAMPLE 5

Synthesis of TRH Analogues of Formula III

Figure 6:
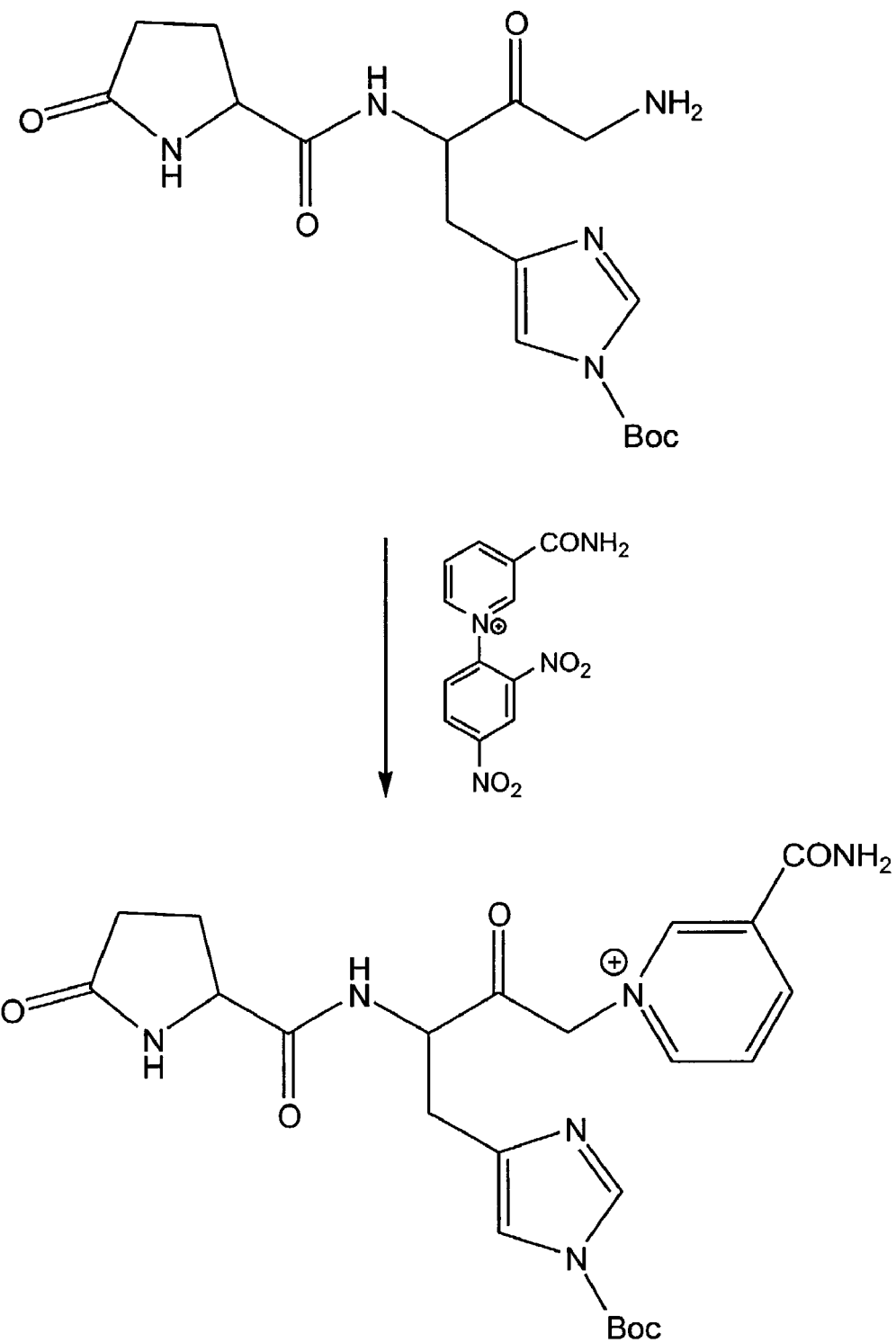
FIG. 6 illustrates illustrates a preparatory scheme for the synthesis of TRH analogues of Formula III.

FIG. 6 illustrates the preparation of TRH analogues of Formula III produced via SPPS synthesis utilizing Fmoc-chemistry. TRH analogues of Formula III are readily synthesized by analogy using the above-described protocols. The completion of the reaction may be monitored by HPLC with UV detection at 355 nm.

Numerous TRH analogues and their respective prodrugs, according to the present invention, as well as related, equivalent compounds, may be readily synthesized by analogy by simply modifying the above-described synthetic pathways, utilizing methods which are known to those of ordinary skill in the art.

The following example describes the increased potency and longer duration of activity of a prodrug form of a TRH analogue according to the present invention.

EXAMPLE 6

Pharmacological Comparison of the Duration of Analeptic Action Between TRH and a Prodrug of a Subject TRH Analogue A pharmacological paradigm was used to assess the potency of the subject TRH analogues as central nervous system agents administered to animals in their prodrug forms in vivo. The antagonism on the barbituate-induced anesthesia was explored to survey the extent of activation of cholinergic neurons by the test compounds. Ten to sixteen Swiss Webster mice (30±2 g) were used in each group. Test compounds were dissolved in degassed DMSO. The vehicle alone (1.5 ml/kg body weight) or equimolar doses of TRH as control and prodrugs according to the present invention (15 μmol/kg body weight) were injected through the tail vein. After 10 minutes, each animal received an intraperitoneal (i.p.) injection of sodium pentobarbital at dose 60 mg/kg bodyweight. An increase in the time after which the animals were injected with TRH and a TRH analogue according to the present invention and after the cholinergic challenge was made was increased. The sleeping time was recorded as the time elapsed from the onset of the loss of righting reflex until the reflex was regained.

Figure 5:
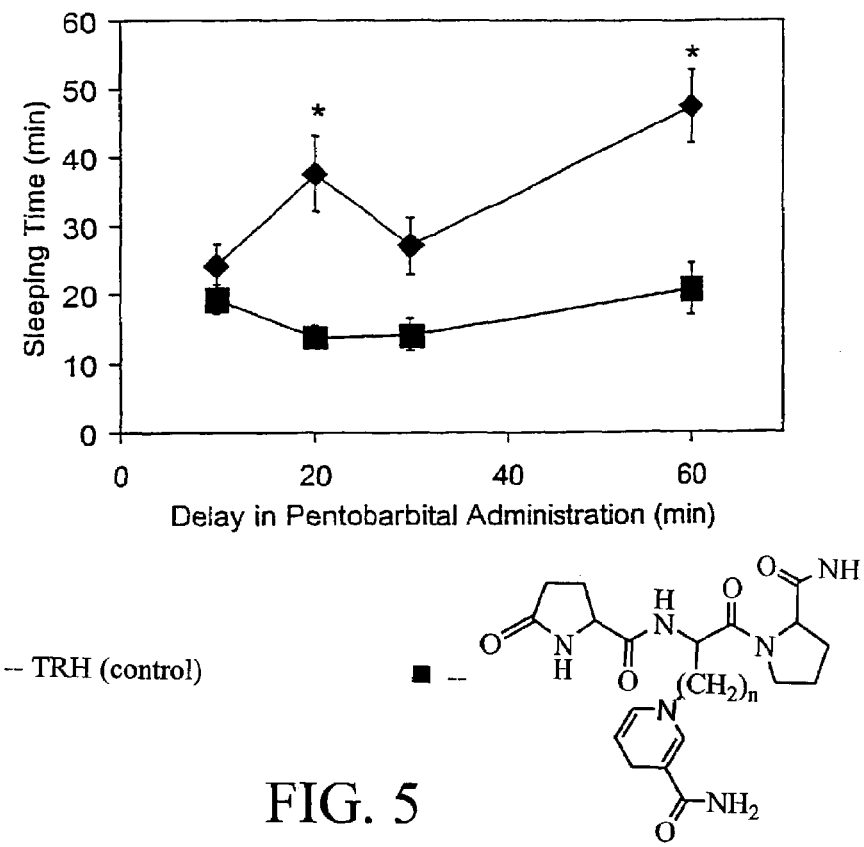
FIG. 5 illustrates the pharmacological comparison of analeptic action between TRH and a prodrug form of a TRII analogue according to the present invention.

The analeptic activity of TRH showed a decrease (in overall trend) when the time between injections was increased, as illustrated in FIG. 5. A loss of over 50% of central nervous system activity was observed at 60 minutes, compared to when pentobarbital injection was made after 10 minutes. The TRH analogue reached its highest analeptic activity 20 to 30 minutes after the administration of its prodrug and remained comparable 60 minutes post-administration to the maximum effect reached by TRH. Such evidence supports the reasoning that the central nervous system effect of TRH dissipated due to its metabolic instability and depletion from the site of action as time elapsed while the TRH analogue prodrug remained trapped in the brain and its enzymatic degradation was slow.

EXAMPLE 7

Pharmacological Comparison of the Analeptic Action in Mice Between TRH and Prodrugs of TRH Analogues of Formula II Further pharmacological studies were performed on TRH analogues of the subject invention, in particular TRH analogues of Formula II. These studies were performed to assess the CNS activity of the compounds of the present invention. Synthesis of the TRH analogues of Formula II and corresponding prodrugs, as illustrated in FIGS. 3B and 3C, were performed using the solid-phase peptide synthesis (SPPS) strategy.

Pre-loaded Fmoc-Pro-Rink Amide-MBHA resin was deprotected with 20% (v/v) piperidine in DMF for 10 minutes, followed by coupling with Fmoc-diaminopropionic/butyric acid, ornithine, or lysine, respectively, protected with Dde (B. Bycroft, et al., *J. Chem. Soc. Chem. Commun.*, 778 (1993))in their side-chain amino group. Once the pyroglutamic acid had been attached, the Dde group was removed by two 5 minute treatments of the resin with 2% hydrazine hydrate in DMF unmasking the side chain amino group for the Zincke-reaction. A Zincke-type salt [N-(2,4-dinitrophenyl)nicotinamide chloride] was initially prepared by heating the mixture of 1-chloro-2,4-dinitrobenzene (1.1 eq) and nicotinamide (1 eq) at 100° C. for 2 hours. After cooling down, MeOH was added and the product was precipitated with ether. This procedure was repeated 3 times. Recrystallization from EtOAc resulted in a pale-yellow solid. To the resin suspended in DMF, 5 eq. of the Zincke-type salt was added in the presence of catalytic amount of pyridine and the mixture was kept at 60° C. The reaction was usually complete within 4–5 hours. TRH analogues according to the present invention are cleaved from the resin using TFA:water (98:2, v/v) and purified by semi-preparative gradient, HPLC on octadecylsilica reversed phase. The completion of the reaction may be monitored by HPLC with UV detection at 254 nm.

Figure 7:
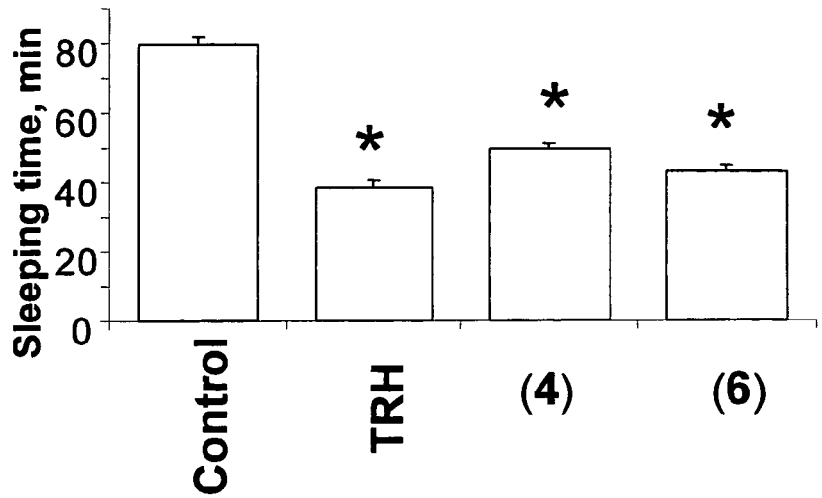
FIG. 7 illustrates the similarity in analeptic activity of TRH and prodrugs of TRH analogues of Formula II in mice.
Figure 7:
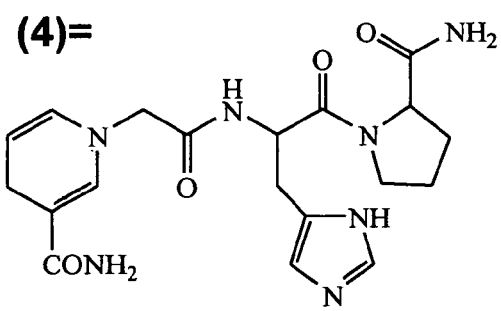
Figure 7:
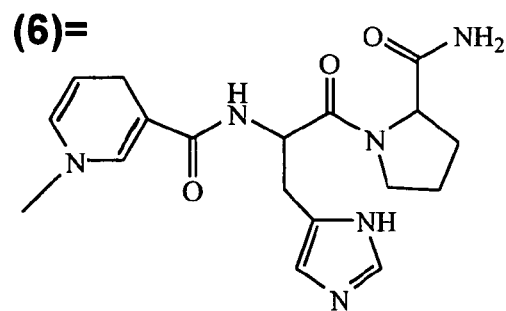

The prodrugs of TRH analogues of Formula II (see FIGS. 3A, 3B, and 3C), TRH, and a saline solution (control) were administered to mice intravenously. The prodrugs of TRH analogues of the invention were injected intravenously into mice at equimolar doses of 10 μmole/kg body weight when pentobarbital (i.p., 60 mg/kg body weight) was given to the mice 10 minutes after the injection of the saline vehicle, TRH, or the prodrugs of TRH analogues. Statistical significance from control ($P<0.05$) was calculated on ANOVA followed by Dunnett's test. As illustrated in FIG. 7, the prodrugs of the TRH analogues of Formula II performed nearly identically to TRH-based on analeptic activity in the mice.

EXAMPLE 8

Affinities of Subject TRH Analogues of Formula I to Lipid Membranes as a Predictor of Transport Across the Blood-brain Barrier A rapid evaluation of the increase of the ability of TRH analogues of Formula I (TRH histidyl portion substituted with ester) according to the present invention to interact with biological membranes was performed by IAMC. This technique measures the partitioning into monolayers of cell membrane phospholipids immobilized by covalent binding on silica particles. The chromatographic capacity factor ($k'_{IAM}$) for a compound obtained by IAMC is directly related to its partition coefficient between the aqueous phase and the chemically bonded membrane phase and, ultimately, to the $K_m$ value representing its fluid-membrane partition coefficient.

An increase in the $k'_{IAM}$ essentially indicates an increase in the membrane permeability of the compound. IAMC mimics membrane interactions better than partitioning in the isotropic n-octanol/water system (log P), and the technique has been applied to the assessment of blood-brain barrier penetration for structurally diverse drugs. The atmospheric-pressure ionizations (APCI) mass spectrometry was employed as a method of detection. The IAMC retention of the TRH analogues of Formula I (in which $R^3$ is an ester moiety) of the present invention was actually lower than that of citric acid, a routinely employed reference as a compound with essentially no affinity to a lipid membrane. Therefore, $k'_{IAM}$ capacity factors [$(t_R-t_0)/t_0$, where $t_R$ is the retention time for the analyte] were calculated with the prodrugs of the present invention as a marker for the dead time ($t_0$).

Figure 8:
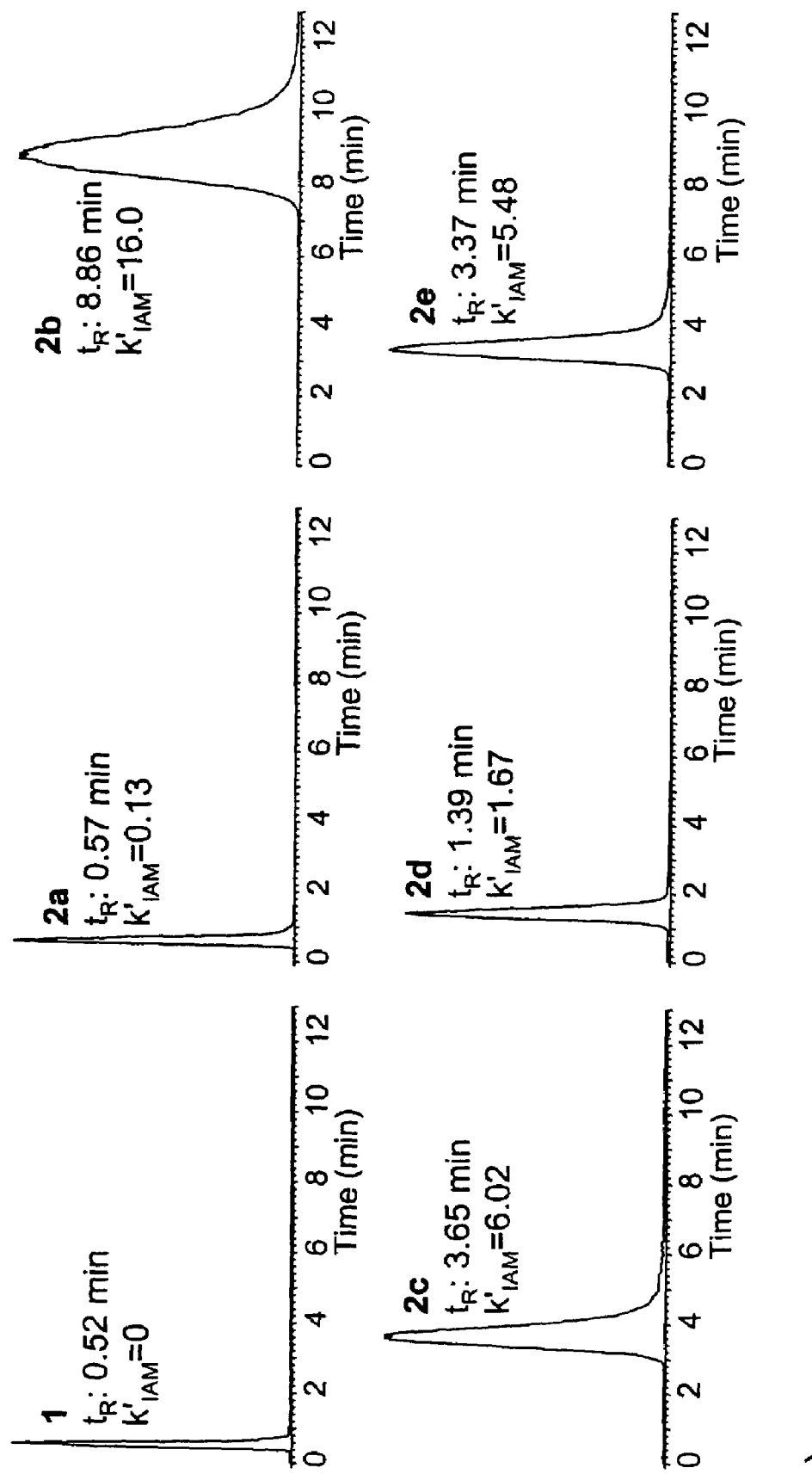
FIG. 8 illustrates graphical activity of TRH analogues of Formula II using immobilized artificial membrane chromatography.

As shown in FIG. 8, the TRH analogues in which $R^3$ is an ester moiety had an increased membrane affinity compared to the parent compound (TRH-like tripeptide pGlu-Glu-Pro-NH$_2$) and the hexyl ester yielded the highest $k'_{IAM}$ (16.0).

EXAMPLE 9

In vitro Study of Analeptic Action in Mice of TRH Analogues of Formula I

In vitro stability studies in mouse brain homogenate (20% w/v) were conducted at 100 μM concentration of TRH analogues of Formula I wherein $R^3$ is an ester moiety. Analytical reversed-phase gradient HPLC with UV detection (λ=214 nm) was used to monitor the decline in the concentration in the compound added. The half-lives ($t_{1/2}$) were 20 and 22 minutes for the TRH analogues derived from primary alcohols and 25 minutes and 70 minute for TRH analogues derived from SPSS. TRH analogues of the subject invention in which $R^3$ is benzyl ester was discovered to be relatively stable in the tissue ($t_{1/2}$>2 hours).

The antagonism of the barbiturate-induced anesthesia in mice was used to assess the increase in the access of the TRH analogues of the present invention to the central nervous system compared to the parent TRH-like tripeptide (pGlu-Glu-Pro-NH$_2$). In this assay related to the analeptic activity of the TRH-like tripeptide, 10 to 18 Swiss Webster mice (30±2 g body weight) were used in each group. The vehicle alone (1.5 ml/kg body weight) or equimolar doses of TRH-like tripeptide as control and the TRH analogues of Formula I (10 μmole/kg body weight) were injected through the tail vein (i.v.). In another group of animals, the TRH-like tripeptide was administered at 10-times higher dose (100 μmol/kg) for comparison. After 10 minutes, each animal received an intraperitoneal (i.p.) injection of sodium pentobarbital at a dose of 60 mg/kg body weight. The sleeping time was recorded from the onset of the loss of righting reflex until the reflex was regained.

Figure 9:
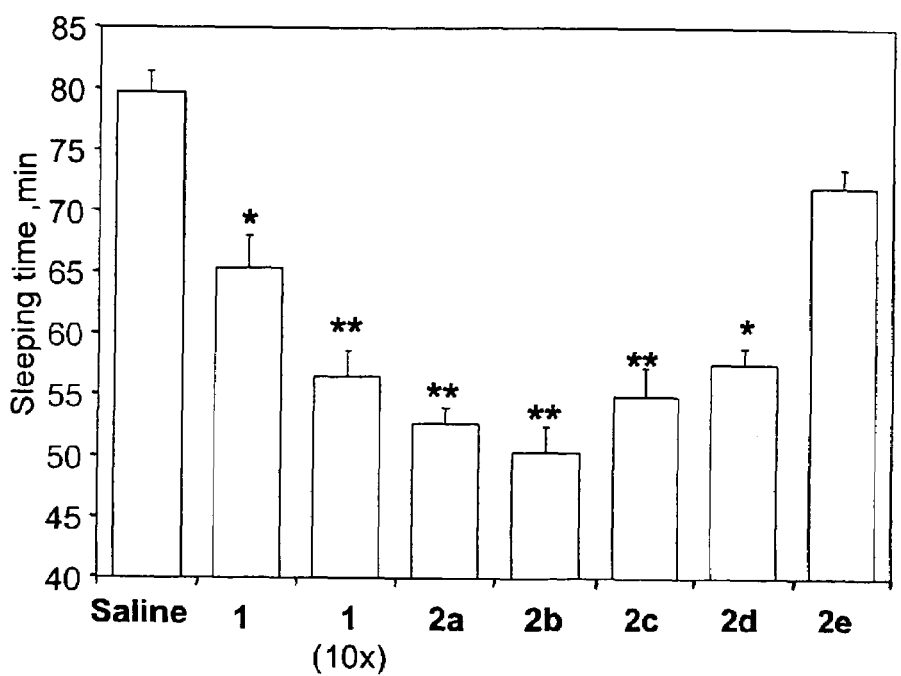
FIG. 9 is a graphical illustration of the analeptic effects of TRH analogues of Formula I on mice as compared to control.

As illustrated in FIG. 9, a significant decrease in the sleeping time was obtained by one-way analysis of variance (ANOVA) followed by post hoc Tukey test (p<0.05) against the control group (animals injected with the vehicle; sleeping time 80±2 minutes SEM, n=18) for all of the tested TRH analogues except TRH analogues of the subject invention in which $R^3$ is benzyl ester. When compared to an equimolar dose of the TRH-like tripeptide, (sleeping time 65±3 minutes SEM), the TRH analogues of Formula I showed a statistically significant decrease. Based on measuring analeptic activity in the animal model selected.

The TRH analogues of the present invention outperformed the TRH-like tripeptide. The measured pharmacological effect appeared to correlate with the metabolic stability of the TRH analogues of Formula I. Specifically, half-lives in mouse brain homogenate around 20–25 minutes yielded an apparently large enhancement in central nervous system delivery. Accordingly, the TRH analogues of the subject invention provide effective access to the brain to exert beneficial therapeutic effects.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A compound having the following structure

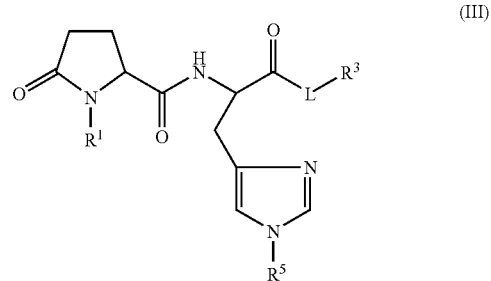

or a pharmaceutically acceptable salt or prodrug thereof, wherein $R^1$ is selected from the group consisting of H, alkyl, aryl, heterocycle, heteroaryl, hydroxyalkyl, alkylaryl, substituted aryl, COX, and COOX, wherein X is selected from the group consisting of alkyl, amine, alkylamino, aryl, substituted aryl, arylalkyl, and acyloxyalkyl;

$R^3$ is 3-($R^1$-)aminocarbonyl-pyridinium-1-yl, where carbon marker 2, 4, 5, or 6 of the pyridinium ring is independently and optionally attached to hydrogen, halogen, isopropyl, alkyl, alkenyl, alkynyl, carbocycle, aryl, heterocycle, heteroaryl, alkylamino, hydroxyalkyl, alkoxyalkyl, amide, CN, or a linear or branched hydrocarbon from 1–15 atoms carbon atoms in length, that can optionally include one or more heteroatoms in the chain;

R[5] is selected from the group consisting of alkyl, 1-Z, and 1H-imidazol-4-ylmethyl (or its tautomeric 1H-imidazol-5-ylmethyl), where Z is selected from the group consisting of H, alkyl, alkyloxycarbonyl, aryl, substituted aryl, arylalkyl, COX, or COOX; and L is selected from the group consisting of alkyl including $(CH_2)_n$, aryl, heterocycle, or heteroaryl, where n is an integer from 0 to 10.

2. A compound, wherein the compound has the following structure

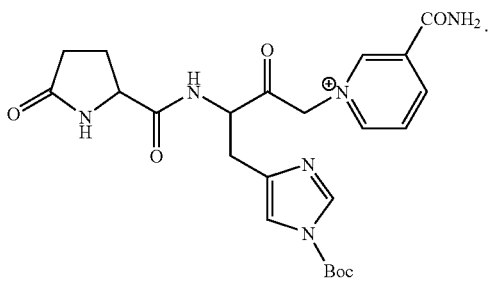

3. A pharmaceutical composition comprising a compound having the following structure

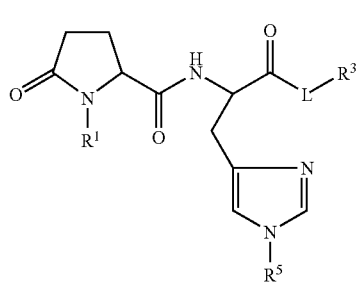

(III)

or a pharmaceutically acceptable salt or prodrug thereof, wherein

R[1] is selected from the group consisting of H, alkyl, aryl, heterocycle, heteroaryl, hydroxyalkyl, alkylaryl, substituted aryl, COX, and COOX, wherein X is selected from the group consisting of alkyl, amine, alkylamino, aryl, substituted aryl, arylalkyl, and acyloxyalkyl;

R[3] is 3-(R[1]-)aminocarbonyl-pyridinium-1-yl, where carbon marker 2, 4, 5, or 6 of the pyridinium ring is independently and optionally attached to hydrogen, halogen, isopropyl, alkyl, alkenyl, alkynyl, carbocycle, aryl, heterocycle, heteroaryl, alkylamino, hydroxyalkyl, alkoxyalkyl, amide, CN, or a linear or branched hydrocarbon from 1–15 atoms carbon atoms in length, that can optionally include one or more heteroatoms in the chain;

R[5] is selected from the group consisting of alkyl, 1-Z, and 1H-imidazol-4-ylmethyl (or its tautomeric 1H-imidazol-5-ylmethyl), where Z is selected from the group consisting of H, alkyl, alkyloxycarbonyl, aryl, substituted aryl, arylalkyl, COX, or COOX;

L is selected from the group consisting of alkyl including $(CH_2)_n$, aryl, heterocycle, or heteroaryl, where n is an integer from 0 to 10; and a pharmaceutically acceptable carrier or diluent.

4. A pharmaceutical composition comprising a compuond having the following structure

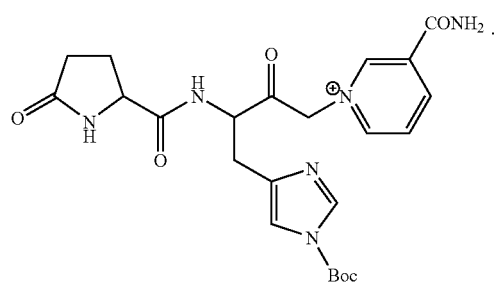

* * * * *

UNITED STATES PATENT AND TRADEMARK OFFICE
CERTIFICATE OF CORRECTION

PATENT NO. : 7,067,257 B2
APPLICATION NO. : 10/419538
DATED : June 27, 2006
INVENTOR(S) : Laszlo Prokai It is certified that error appears in the above-identified patent and that said Letters Patent is hereby corrected as shown below:

Column 6,
Line 11, "of a TRII" should read --of a TRH--.

Column 23,
Line 7, "or heteroaryl" should read --and heteroaryl--.

Column 24,
Line 19, "or COOX" should read --and COOX--.

Line 21, "or heteroaryl" should read --and heteroaryl--.

Signed and Sealed this

Twenty-eighth Day of November, 2006

JON W. DUDAS
*Director of the United States Patent and Trademark Office*